United States Patent
Tanaka et al.

(10) Patent No.: US 11,141,212 B2
(45) Date of Patent: Oct. 12, 2021

(54) SURGICAL OPERATION SYSTEM

(71) Applicant: OLYMPUS CORPORATION, Tokyo (JP)

(72) Inventors: Kazue Tanaka, Sagamihara (JP); Takashi Mihori, Akiruno (JP); Yoshitaka Honda, Hachioji (JP); Ryoichi Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 969 days.

(21) Appl. No.: 15/832,072

(22) Filed: Dec. 5, 2017

(65) Prior Publication Data

US 2018/0111009 A1    Apr. 26, 2018

Related U.S. Application Data

(63) Continuation of application No. 13/791,933, filed on Mar. 9, 2013, now Pat. No. 9,878,183, which is a (Continued)

(51) Int. Cl.
*A61B 18/14* (2006.01)
*A61B 18/12* (2006.01)
(Continued)

(52) U.S. Cl.
CPC ...... *A61B 18/1402* (2013.01); *A61B 18/1206* (2013.01); *A61B 2017/320069* (2017.08); (Continued)

(58) Field of Classification Search
CPC ............ A61B 18/1206; A61B 18/1402; A61B 2018/00845; A61B 2018/00869; A61B 2017/320069; A61B 2017/320082
See application file for complete search history.

(56) References Cited

U.S. PATENT DOCUMENTS 6,113,593 A    9/2000 Tu et al.
2004/0015065 A1    1/2004 Panescu et al.
(Continued)

FOREIGN PATENT DOCUMENTS

EP    2 138 123 A1    12/2009
JP    2000-271145 A    10/2000
(Continued)

OTHER PUBLICATIONS

Extended Supplementary European Search Report dated Mar. 5, 2015 received in 12832809.3.
(Continued)

*Primary Examiner* — Michael F Peffley
*Assistant Examiner* — Samantha M Good
(74) *Attorney, Agent, or Firm* — Scully, Scott, Murphy & Presser, P.C.

(57) ABSTRACT

A surgical operation system includes a US signal output section, an HV signal output section, a probe having a treatment section which has an HV signal applied thereto and vibrates by ultrasound, an HV signal main controller that performs feedback control of the HV signal output section based on the HV signal, a US signal main controller that performs feedback control of the US signal output section based on a US signal, and an HV signal auxiliary controller that controls the HV signal output section based on the US signal, and has a response time shorter than that of the HV signal main controller.

4 Claims, 14 Drawing Sheets

Related U.S. Application Data continuation of application No. PCT/JP2012/070891, filed on Aug. 17, 2012.

(60) Provisional application No. 61/536,779, filed on Sep. 20, 2011, provisional application No. 61/536,796, filed on Sep. 20, 2011, provisional application No. 61/536,818, filed on Sep. 20, 2011.

(51) Int. Cl.
*A61B 17/32* (2006.01)
*A61B 90/00* (2016.01)
*A61B 18/00* (2006.01)

(52) U.S. Cl.
CPC ............ *A61B 2017/320082* (2017.08); *A61B 2018/00845* (2013.01); *A61B 2018/00869* (2013.01); *A61B 2018/00928* (2013.01); *A61B 2090/065* (2016.02)

(56) References Cited

U.S. PATENT DOCUMENTS

| | | |
|---|---|---|
| 2005/0203504 A1 | 9/2005 | Wham et al. |
| 2009/0326569 A1 | 12/2009 | Tanaka et al. |

FOREIGN PATENT DOCUMENTS

| | | |
|---|---|---|
| JP | 2002-306507 A | 10/2001 |
| JP | 2010-5370 A | 1/2010 |
| WO | 2012/033974 A2 | 3/2012 |

OTHER PUBLICATIONS

International Search Report and Written Opinion dated Sep. 11, 2012 received in PCT/JP2012/070891.
US OA dated Dec. 3, 2014 received in U.S. Appl. No. 13/791,933.
US Final OA dated Apr. 17, 2015 received in U.S. Appl. No. 13/791,933.
US OA dated Jun. 30, 2016 received in U.S. Appl. No. 13/791,933.
US Final OA dated Dec. 1, 2016 received in U.S. Appl. No. 13/791,933.

SURGICAL OPERATION SYSTEM

CROSS REFERENCE TO RELATED APPLICATION

This application is a continuation application of U.S. Ser. No. 13/791,933 filed on Mar. 9, 2013, issued as U.S. Pat. No. 9,878,183, which is a continuation application of PCT/JP2012/070891 filed on Aug. 17, 2012 and claims benefit of U.S. Provisional Patent Application Nos. 61/536,779 filed in the U.S.A. on Sep. 20, 2011, 61/536,796 filed in the U.S.A. on Sep. 20, 2011, 61/536,818 filed in the U.S.A. on Sep. 20, 2011, the entire contents of each of which are incorporated herein by reference.

BACKGROUND OF THE INVENTION

1. Field of the Invention

The present invention relates to a surgical operation system including a handpiece to which ultrasound energy and high-frequency energy are simultaneously applied.

2. Description of the Related Art

In a surgical operation, a monopolar type handpiece using a high-frequency current is used when cutting or coagulation of living tissue is performed. A cutting mode in which cutting is performed, and a coagulation mode in which coagulation is performed are switched by a waveform of the high-frequency current which is applied to a treatment section 9 of the handpiece. In the cutting mode, a high-frequency current (high-frequency energy) of a continuous waveform is applied, and living tissue is transpired by large heat generation. In the coagulation mode, a high-frequency current of an interrupted wave (burst wave) is applied, and thereby living tissue is kept at a temperature at which protein and the like are coagulated. In a blend mode in which a high-frequency current of a current waveform with the continuous waveform and the burst waveform being blended, bleeding can be stopped while living tissue is cut.

Japanese Patent Application Laid-Open Publication No. 2002-306507 discloses that living tissue is prevented from being burnt onto the treatment section 9 by application of not only a high-frequency current but also ultrasound vibration to the treatment section 9.

Further, Japanese Patent Application Laid-Open Publication No. 2010-5370 discloses a surgical operation system which detects ultrasound impedance corresponding to the ultrasound vibration of the treatment section 9 to which a high-frequency current and ultrasound vibration are applied, and controls the high-frequency current.

Here, the effect of the conventional surgical operation system including the handpiece to which a high-frequency current and ultrasound vibration are applied is only simple addition of the effect obtained by application of only the high-frequency current and the effect obtained by application of only the ultrasound vibration.

SUMMARY OF THE INVENTION

A surgical operation system of an embodiment includes a drive signal output section that outputs a drive signal, a high-frequency signal output section that outputs a high-frequency signal, a probe having a treatment section with the high-frequency signal being applied thereto, that vibrates by ultrasound that an ultrasound transducer generates by the drive signal, and performs a bleeding stopping process while making an incision line in a pressing direction, when the probe is pressed against a parenchyma organ by a synergetic effect of the drive signal and the high-frequency signal, a counter electrode plate that forms a return circuit of the high-frequency signal, a high-frequency signal main control section that performs feedback control of the high-frequency signal output section, based on the high-frequency signal, a drive signal main control section that performs feedback control of the drive signal output section, based on the drive signal, a high-frequency signal auxiliary control section that controls the high-frequency signal output section to stop output of the high-frequency signal based on the drive signal, and has a response time shorter than that of the high-frequency signal main control section.

A surgical operation system of another embodiment includes a treatment section that is a treatment section that simultaneously performs a high-frequency treatment and an ultrasound treatment on tissue, and performs a bleeding stopping process while making an incision line on the tissue, a drive signal output section that outputs a drive signal for the ultrasound treatment to the treatment section, a drive signal detection section that detects a parameter of the drive signal which the drive signal output section outputs, a drive signal main control section that performs feedback control of the drive signal output section based on the parameter which is detected in the drive signal detection section, a high-frequency signal output section that outputs a high-frequency signal for the high-frequency treatment to the treatment section, a high-frequency signal detection section that detects a parameter of the high-frequency signal which the high-frequency signal output section outputs, a drive signal main control section that performs feedback control of the high-frequency signal output section based on the parameter which is detected in the high-frequency signal detection section, a high-frequency signal auxiliary control section that determines whether or not the treatment section separates from the tissue based on the parameter detected in the drive signal detection section, and controls the high-frequency signal output section to stop output of the high-frequency signal when the high-frequency signal auxiliary control section determines that the treatment section separates from the tissue, and has a response time shorter than that of the high-frequency signal main control section, and a recovery section that forms a return circuit of the high-frequency signal outputted to the treatment section.

DETAILED DESCRIPTION OF THE PREFERRED EMBODIMENTS

First Embodiment

Figure 1:
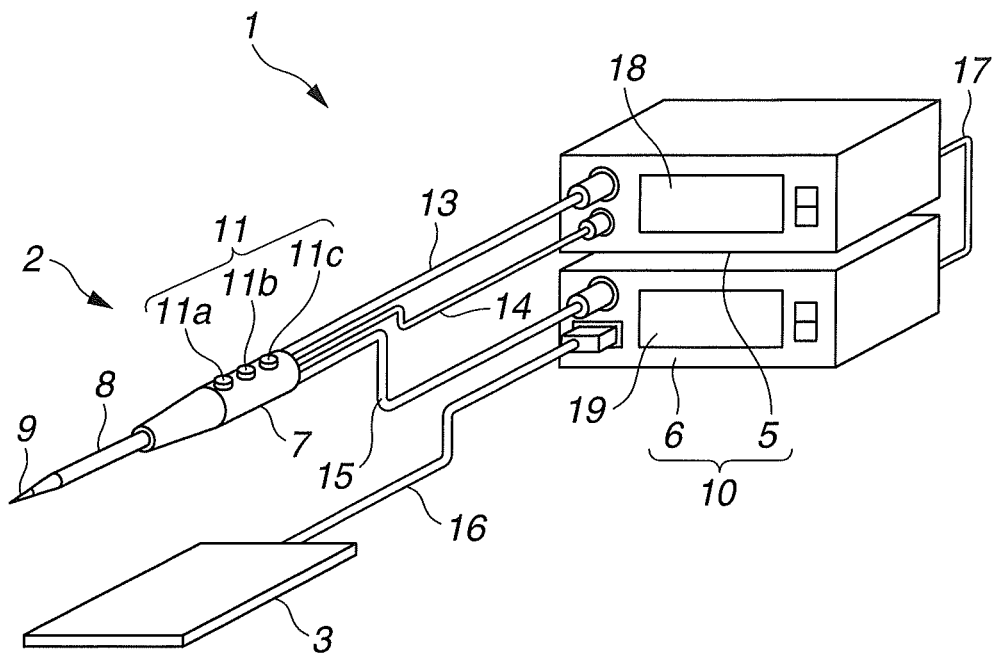
FIG. 1 is a perspective view showing an entire configuration of a surgical operation system of a first embodiment.

Hereinafter, a surgical operation system 1 of a first embodiment of the present invention will be described with reference to the drawings. As shown in FIG. 1, the surgical operation system 1 includes a handpiece 2, an ultrasound transducer drive signal generating apparatus (hereinafter, called "US apparatus") 5, a high-frequency current signal generating apparatus (hereinafter, called "HV apparatus") 6, and a counter electrode plate 3 as a recovery section. Note that the US apparatus 5 and the HV apparatus 6 may be a signal generating apparatus 10 in which the US apparatus 5 and the HV apparatus 6 are housed in one casing and share some functions.

Outline of the Surgical Operation System

The monopolar type handpiece 2 is a surgical treatment instrument having a treatment section 9 at a distal end. The US apparatus 5 generates a drive signal (hereinafter, called "US signal") that drives an ultrasound transducer 23 (see FIG. 2) contained in the handpiece 2. The HV apparatus 6 supplies a high-frequency signal (hereinafter, called "HV signal") to the handpiece 2. As will be described later, the counter electrode plate 3 that is the recovery section is disposed to be in contact with a hip or the like of a patient in a large area, and forms a return circuit of the HV signal.

The handpiece 2 has a grasping portion 7 for a surgeon to grasp, a shaft portion 8 that protrudes forward from the grasping portion 7, and a treatment section 9 placed at a distal end of the shaft portion 8. On the grasping portion 7, a selection switch 11 (11a, 11b, 11c) for performing selection or the like of a treatment that is performed with the treatment section 9 is placed.

From a rear end side of the grasping portion 7 of the handpiece 2, a US cable 13, a hand switch cable 14, and an HV cable 15 are extended. In the US cable 13 and the hand switch cable 14, connectors at end portions thereof are detachably connected to the US apparatus 5. In the HV cable 15, a connector at an end portion thereof is detachably connected to the HV apparatus 6. To the HV apparatus 6, a connector of an end portion of a counter electrode plate cable 16 that is connected to the counter electrode plate 3 is also detachably connected. The US apparatus 5 and the HV apparatus 6 perform transmission and reception of signals via a communication cable 17 which is connected thereto. Further, the US apparatus 5 and the HV apparatus 6 respectively have front panels 18 and 19 for performing display and operation input. The US apparatus 5 and the HV apparatus 6 may be operable by foot switches or the like.

Figure 2:
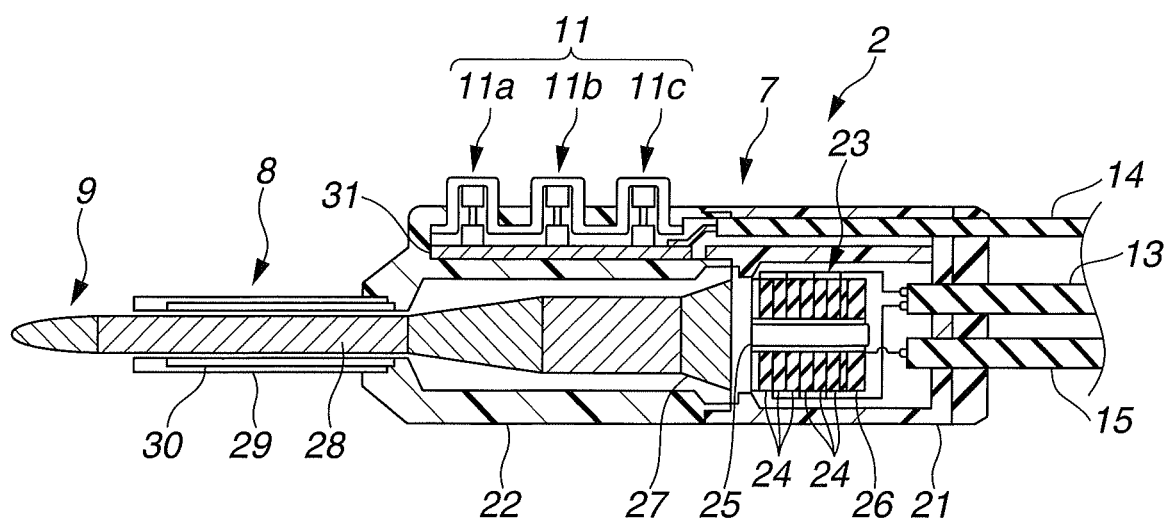
FIG. 2 is a sectional view showing an internal configuration of a handpiece of the surgical operation system of the first embodiment.

As shown in FIG. 2, in the handpiece 2, a housing portion is configured by a substantially cylindrical main case 21 that configures the grasping portion 7, and a secondary case 22 connected to an end portion thereof. Inside the main case 21, the ultrasound transducer (US transducer) 23 connected to the US cable 13 is disposed.

The ultrasound transducer 23 includes a plurality of ring-shaped electrostrictive elements 24 that are fastened by a bolt 25 and a nut 26. When the US signal is applied to electrodes that are provided on respective surfaces of the electrostrictive elements 24, the ultrasound transducer 23 performs ultrasound vibration. The ultrasound vibration is transmitted to the treatment section 9 through the shaft portion 8 that is configured by a horn 27 connected to a front end of the ultrasound transducer 23 (bolt 25) and a probe 28. Note that the probe 28 is inserted through an inside of a metallic pipe 30 that is covered with an insulating pipe 29.

The nut 26 is made of a metal, and is also a conductive portion to which a conductor wire of the HV cable 15 is connected. The HV signal that is applied to the nut 26 is transmitted to the treatment section 9 made of a metal through the bolt 25 made of a metal and the probe 28 made of a metal.

Configuration of the Surgical Operation System

Figure 3:
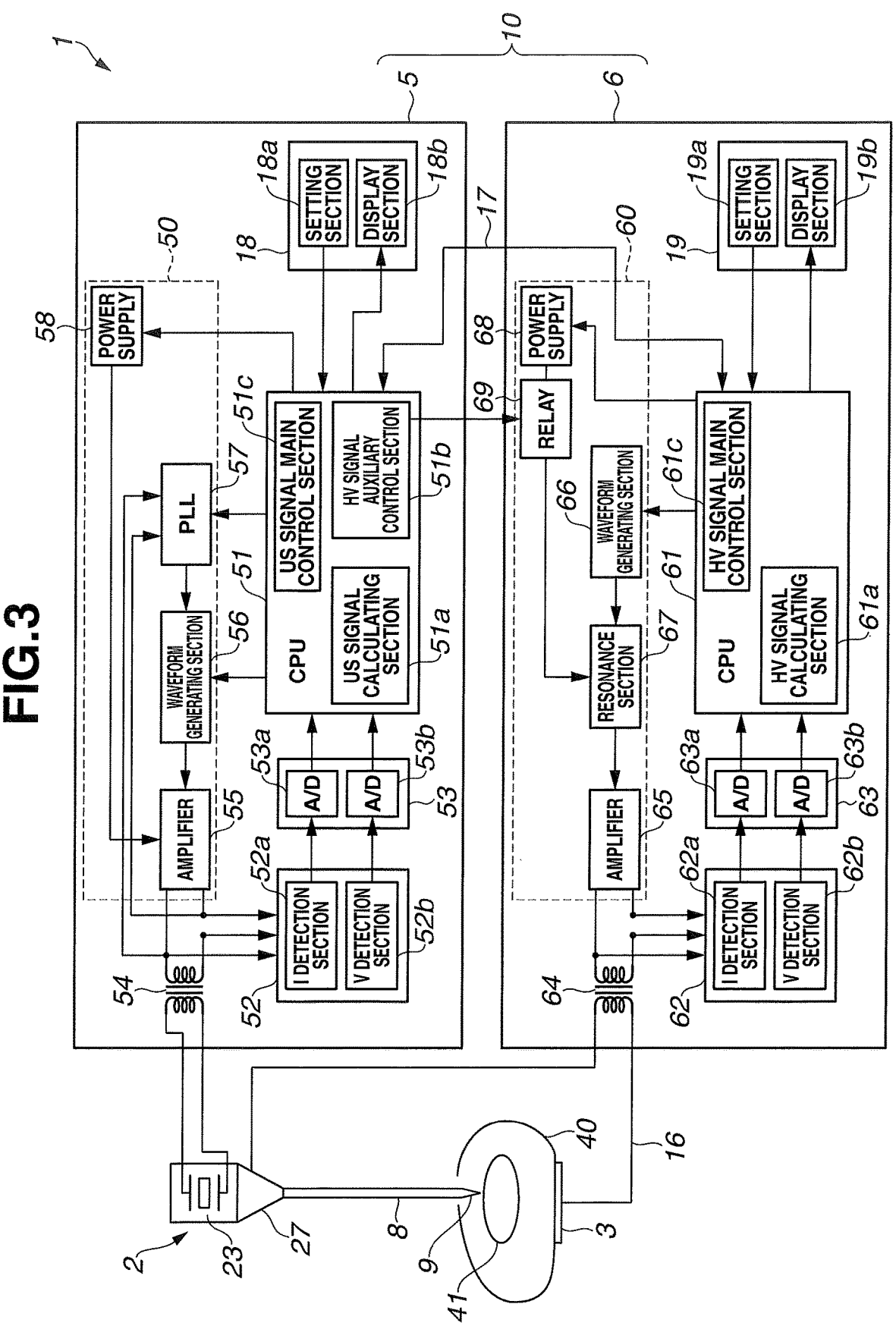
FIG. 3 is a configuration diagram showing a configuration of a surgical operation system of the first embodiment.

Next, a configuration of the surgical operation system 1 will be described with use of FIG. 3. A surgeon performs processing of making an incision line on an organ 41 of a patient 40 with use of the treatment section 9 of the handpiece 2 of the surgical operation system 1.

The US apparatus 5 which generates a US signal to supply ultrasound (US) energy to the treatment section 9 has a central processing unit (CPU) 51, a US signal detection section 52, an A/D conversion section 53, an output transformer 54, an amplifier 55, a waveform generating section 56, a PLL section 57 and a power supply 58. The output transformer 54, the amplifier 55, the waveform generating section 56, the PLL section 57 and the power supply 58 configure a drive signal output section (US signal output section) 50. The US signal is, for example, an AC signal of a sine wave of a predetermined fundamental frequency (resonance frequency).

The CPU 51 which performs control of the entire US apparatus 5 has a drive signal calculating section (US signal calculating section) 51a, a drive signal main control section (US signal main control section) 51c and a high-frequency signal auxiliary control section (HV signal auxiliary control section) 51b. Note that the US signal calculating section 51a, the US signal main control section 51c and the HV signal auxiliary control section 51b may be respectively configured by different CPUs.

The waveform generating section 56 generates, for example, a sine-wave signal. The sine-wave signal generated by the waveform generating section 56 is amplified in the amplifier 55, thereafter is applied to a primary winding side of the output transformer 54, and is applied to the ultrasound transducer 23 of the handpiece 2 as the US signal from an output terminal at a secondary winding side of the output transformer 54.

A US signal intensity, that is, the ultrasound output of the ultrasound transducer 23 is regulated in accordance with an output voltage of the power supply 58. The output voltage of the power supply 58, that is, the ultrasound output and an operation of the waveform generating section 56 are controlled by the US signal main control section 51c.

The US signal main control section 51c controls the output voltage and the like of the power supply 58 so as to produce ultrasound output corresponding to a setting operation based on the US signal (parameter) which the US signal detection section 52 detects, in response to the setting operation by a setting section 18a or the like of the front panel 18. The front panel 18 is provided with a display section 18b that displays information such as the US signal intensity which is outputted from the CPU 51. Namely, the US signal main control section 51c performs feedback control.

Further, the sine-wave signal amplified by the amplifier 55 is inputted in a current (I) detection section 52a and a voltage (V) detection section 52b that configure the US signal detection section 52. Further, the sine-wave signal is inputted in the PLL section 57.

The PLL section 57 performs PLL control of the ultrasound transducer 23 so as to cause the ultrasound transducer 23 to drive by the US signal of the resonance frequency. Further, the PLL section 57 performs control so that a phase of the voltage of the US signal becomes the same phase as a phase of the current. An operation of the PLL section 57 is controlled by the US signal main control section 51c.

The US current signal detection section 52a and the US signal voltage detection section 52b converts the sine-wave signal amplified by the amplifier 55 into a root mean square value (RMS). A root mean square value of the voltage and a root mean square value of the current are respectively converted into digital signals by the A/D conversion section 53 (53a, 53b), and are inputted in the CPU 51. The US signal calculating section 51a calculates a US signal intensity (US signal output) with use of a digital signal of the voltage root mean square value or the current root mean square value which is inputted.

The HV apparatus 6 which generates an HV signal and supplies high-frequency (HV) energy to the treatment section 9 has a central processing unit (CPU) 61, an HV signal detection section 62, an A/D conversion section 63, an output transformer 64, an amplifier 65, a waveform generating section 66, a resonance section 67, a power supply 68, and a high-frequency signal relay (HV signal relay) 69. The amplifier 65, the waveform generating section 66, the resonance section 67, the power supply 68 and the HV signal relay 69 configure a high-frequency signal output section (HV signal output section) 60. The HV signal is, for example, an AC signal of a sine wave of a predetermined fundamental frequency.

The HV signal relay 69 is a switch that turns on/off the output of a signal received from the power supply 68 to a post-stage circuit. That is to say, the HV signal relay 69 outputs a signal to the post-stage circuit in an ON state (continuity state), but does not output a signal to the post-stage circuit in an OFF state (open state).

The CPU 61 which performs control of the entire HV apparatus 6 has a high-frequency signal calculating section (HV signal calculating section) 61a and a high-frequency signal main control section (HV signal main control section) 61c. Note that the HV signal calculating section 61a and the HV signal main control section 61c may be respectively configured by different CPUs. Further, the CPU 61 may be the same CPU as the CPU 51.

Figure 4A:
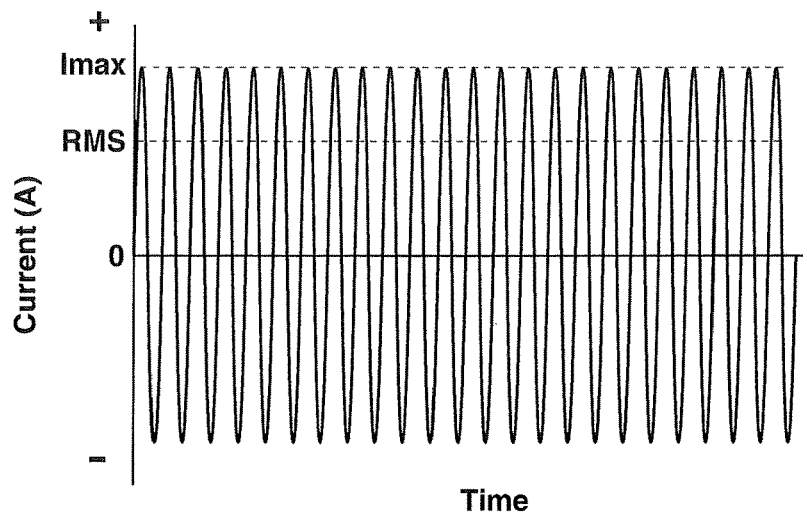
FIG. 4A is an explanatory diagram for explaining a high-frequency signal of a cutting waveform.
Figure 4B:
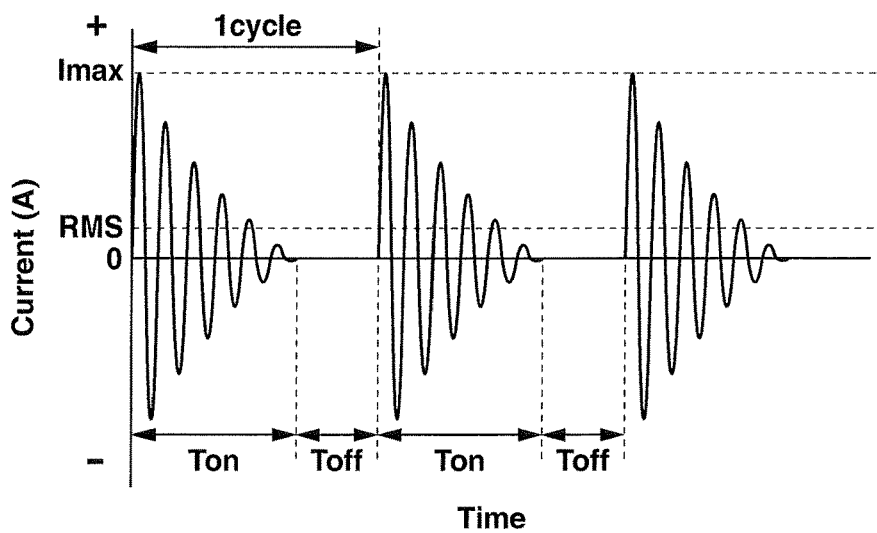
FIG. 4B is an explanatory diagram for explaining a high-frequency signal of a coagulation waveform.

The waveform generating section 66 generates at least a coagulation waveform signal. Whereas the cutting waveform signal of a continuous waveform including a continuous sine wave signal shown in FIG. 4A, the coagulation waveform signal shown in FIG. 4B is an interrupted wave, in which a burst wave is repeated, which has one cycle configured by an attenuating sine-wave signal time period (Ton) in which a maximum value (amplitude) is gradually decreasing, and a signal stopping time period (Toff).

The signal which is outputted from the waveform generating section 66 is inputted in the amplifier 65 via the resonance section 67. The signal amplified by the amplifier 65 is applied to a primary winding side of the output transformer 64, and an HV signal is generated at a secondary winding side.

One end of the secondary winding of the output transformer 64 is continued to the horn 27 and the like of the handpiece 2. Further, the other end of the secondary winding is continued to the counter electrode plate 3 which is in contact with the patient 40 in a wide area.

Further, the resonance section 67 is supplied with electric power from the power supply 68 with a variable voltage. The waveform generating section 66 and the power supply 68 are controlled by the HV signal main control section 61c.

The HV signal main control section 61c controls an output voltage of the power supply 68 and regulates HV signal output, based on the HV signal (parameter) which the HV signal detection section 62 detects, in response to a setting operation by a setting section 19a or the like of the front panel 19. That is to say, the HV signal main control section 61c performs feedback control. Note that the CPU 61 also can variably control a crest factor CF by changing an amplitude, and an attenuation pattern of the sine wave configuring the coagulation waveform and/or the signal stopping time period (Toff) in the case of coagulation waveform signal generation. The crest factor (CF: crest factor) is maximum value (Imax)/root mean square value (RMS), and for example, in a continuous sine wave, CF=1.4.

The front panel 19 is provided with a display section 19b that displays information of the HV signal. The signal amplified by the amplifier 65 is inputted in a current (I) detection section 62a and a voltage (V) detection section 62b that configure the HV signal detection section 62. The HV signal detection section 62 converts the signal which is amplified by the amplifier 65 into a root mean square value. The root mean square value of the voltage and the root mean square value of the current are respectively converted into digital signals by the A/D conversion section 63 (63a, 63b), and are inputted in the CPU 61.

The HV signal calculating section 61a calculates HV signal output by using the inputted digital signal of the voltage root mean square value or the current root mean square value.

The feedback control which is ordinary control performed by the US signal main control section 61c and the HV signal main control section 51c is control for keeping, for example, a signal intensity at a predetermined intensity. In contrast with this, the HV signal auxiliary control section 51b controls the HV signal relay 69 of the HV signal output section 60 into an ON state or an OFF state, based on the US signal detected by the US signal detection section 52. That is to say, the control which is performed by the HV signal auxiliary control section 51b is ON/Off control that only stops output of a signal, and therefore, high-speed control with a short response time can be realized relatively easily as compared with the ordinary control that increases and decreases output.

Here, in the treatment (an ultrasound treatment and a high-frequency treatment) that is performed by ultrasound vibration and a high-frequency current being simultaneously applied to the treatment section, there is the fear of occurrence of a spark discharge (hereinafter, called "high-energy discharge") with large energy that hardly occurs in the treatment (high-frequency treatment) which is performed only a high-frequency current being applied to the treatment section.

For example, when the treatment section 9 separates from the tissue including fat which the treatment section 9 treats, a high-energy discharge is likely to occur to accelerate deterioration of the treatment section 9.

Therefore, the conventional surgical operation system in which ultrasound vibration and a high-frequency current are simultaneously applied to the treatment section needs to be operated by a surgeon with scrupulous care, and cannot be always said as favorable in operability.

Further, in the surgical operation system 1, when the HV signal auxiliary control section 51b senses that the treatment section 9 separates from tissue, based on the US signal detected by the US signal detection section 52, the HV signal auxiliary control section 51b controls the HV signal relay 69 of the HV signal output section 60 into an OFF state. Namely, after an extremely short time period after detection of the US signal, application of the HV signal to the treatment section 9 stops. Therefore, even when the treatment section 9 separates from the tissue, a high-energy discharge does not occur.

It is conceivable that immediately before a high-energy discharge occurs, a discharge that has a small intensity, but differs from an ordinary discharge occurs as a precursory phenomenon thereof. The HV signal auxiliary control section 51b stops output before a high-energy discharge occurs based on the signal change due to the precursory phenomenon or the like, and thereby prevents occurrence of the high-energy discharge.

Namely, in a strict sense, "when the treatment section 9 separates from tissue" does not mean "when the treatment section 9 completely separates", but rather means "when the treatment section 9 starts to separate".

In addition, the HV signal auxiliary control section 51b has a response time shorter than the HV signal main control section 51c. Namely, response times of the US signal main control section 51c and the HV signal main control section 61c which perform feedback control are preferably 5 ms (milliseconds) or longer, and, for example, 100 ms.

In contrast with this, the response time of the HV signal auxiliary control section 51b is preferably 1 ms or less, and, for example, 0.5 ms. Further, the HV signal relay 69 is also the circuit of a simple operation that is an ON/Off operation, and therefore, a response time thereof is 1 ms or less, and is, for example, 0.2 ms. The HV signal relay 69 may be a mechanical type switch, or a semiconductor switch.

Note that if the response time is 1 ms or less, an attenuation section that reduces signal output to substantially zero, namely, reduces a signal intensity to such an intensity that does not influence a treatment or the like may be used in place of the relay type ON/OFF switch. For example, when the amplifier 65 is controllable at a high speed, the function of the attenuation section may be realized by control of the amplifier 65. Namely, in the following description and the like, "stops signal output" is the concept also including the case of "reducing signal output to substantially zero". For example, if the voltage is 200 Vp or less in the HV signal, a medical effect is not exhibited in living tissue, and a high-energy discharge does not occur. However, a relay is the most preferably used, because the relay is a less expensive switch with a high response speed.

Note that the US signal detection section 52 detects signals at intervals of 1 ms or less. The HV signal auxiliary control section 51b sequentially processes the signals which the US signal detection section 52 detects at intervals of 1 ms or less, but the US signal main control section 51c processes the signals which the US signal detection section 52 detects at predetermined intervals longer than the detection intervals of the US signal detection section 52, for example, at intervals of 100 ms. The US signal main control section 51c may perform control with use of an integrated value or a mean value of the signals which the US signal detection section 52 detects at intervals of 1 ms or less.

The HV signal main control section 61c processes the signal which the HV signal detection section 62 detects at intervals of 100 ms, for example.

Figure 5:
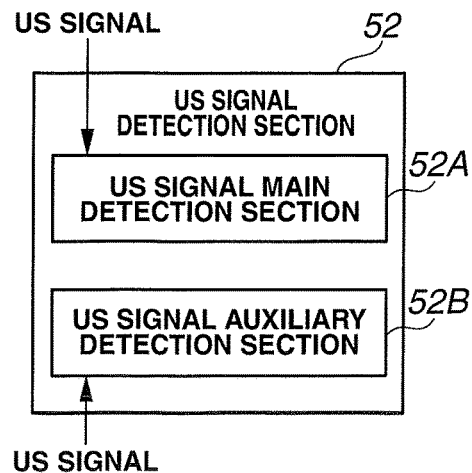
FIG. 5 is a configuration diagram showing a configuration of a signal detection section of the surgical operation system of the first embodiment.

Note that as shown in FIG. 5, the US signal detection section 52 may have a US signal main detection section 52A and a US signal auxiliary detection section 52B. Further, the US signal detected by the US signal main detection section 52A and the US signal detected by the US signal auxiliary detection section 52B may be sampled from the same spot on the circuit, or may be sampled from different spots.

The US signal auxiliary detection section 52B has detection intervals shorter than the US signal main detection section 52A. For example, whereas the US signal main detection section 52A detects signals at intervals of 5 ms or more, for example, intervals of 100 ms, the US signal auxiliary detection section 52B detects signals at intervals of 1 ms or less, for example, intervals of 0.5 ms.

Subsequently, the HV signal main control section 61c performs ordinary feedback control based on the signal detected by a HV signal main detection section 62A, and the HV signal auxiliary control section 51b performs high-speed control with a high response speed based on the signal which the US signal auxiliary detection section 52B detects. Further, the US signal main control section 51c performs ordinary feedback control based on the signal which the US signal main detection section 52A detects.

The US signal main control section 51c and the HV signal main control section 61c can stably perform control if a loop processing time period of detection/response is in the aforementioned range or more. Namely, if the detection interval and the response time are too short in control of feedback, signal output is sometimes excessively increased in response to a noise signal which appears in a pulse form, for example. Therefore, the signal detection intervals and the response times of the US signal main control section 51c and the HV signal main control section 61c are preferably in the aforementioned range or more.

In contrast with this, the HV signal auxiliary control section 51b needs to stop output of the HV signal before a high-energy discharge occurs, when the treatment section 9 contacts other instruments made of metal.

Therefore, the time period from detection of a US signal until an operation of the HV signal relay 69 is completed by control of the HV signal auxiliary control section 51b is preferably 1 ms or less.

If the time period is the above described time period or less, occurrence of a high-energy discharge can be reliably prevented.

Note that the above described detection intervals, the above described response time and the time period until operation completion are preferably short, but in industrially available systems, approximately 1µ (microsecond) is a lower limit value.

Treatment by the Surgical Operation System

At a time of a treatment, the US signal subjected to feedback control by the US signal main control section 51c is applied to the ultrasound transducer 23, and the treatment section 9 performs ultrasound vibration. Subsequently, when the treatment section 9 comes into contact with or comes close to the organ 41 of a treatment target of the patient 40, the HV signal (high-frequency current) which is subjected to feedback control by the HV signal main control section 61c flows from the treatment section 9 to the organ 41. Subsequently, the HV signal which flows into the organ 41 returns to the HV apparatus 6 through an inside of a body of the patient 40, the counter electrode plate 3, and the counter electrode plate cable 16.

The HV energy is applied to the treatment target as Joule heat due to contact resistance and the like of the treatment section 9 and the organ 41, or heat and shock waves due to a discharge phenomenon between the treatment section 9 and the organ 41.

Note that the above described components do not have to be the components (circuits and the like) which are respectively independent, and may be function sections which the CPUs 51 and 61 execute by read programs.

Figure 6:
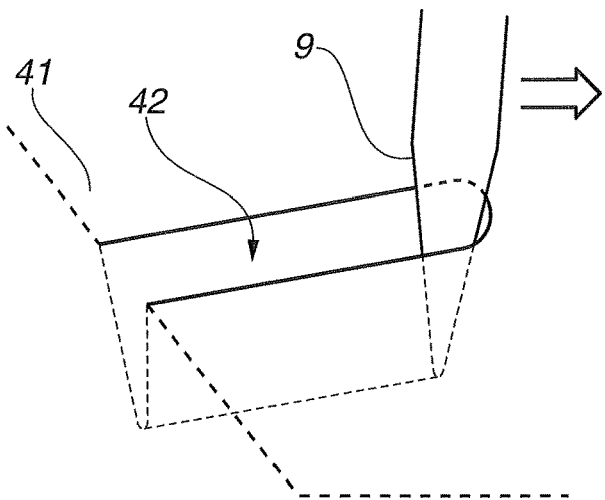
FIG. 6 is a perspective view for explaining processing of making an incision line according to the surgical operation system of the first embodiment.

Next, a treatment by the surgical operation system 1 will be described. As shown in FIG. 6, in the surgical operation system 1, a surgeon performs operation of pressing the treatment section 9 to the organ 41 which is a parenchyma organ while simultaneously applying the HV signal and the US signal to the treatment section 9 of the handpiece 2, and thereby can stop bleeding while the surgeon makes an incision line 42 in a pressing direction.

In contrast with this, in the conventional surgical operation system, it is not easy to stop bleeding while making an incision line on a parenchyma organ having a number of blood vessels therein, for example, a liver, even in the blend mode, and operability cannot be always said as favorable.

Here, "parenchyma organ" refers to tissue in a living body, for example, an organ such as a liver. Further, the medical term "cut" includes three treatments that are "excision", "exfoliation" and "making an incision line".

"Excision" of a polyp or the like or "exfoliation" of a diaphragm or the like corresponds to cutting that cuts off tissue, and therefore, energy can be concentrated into a spot to be cut by the tissue to be cut being sandwiched and grasped. For example, with a handpiece having a jaw that sandwiches and grasps tissue in cooperation with a probe distal end portion to which only ultrasound energy is applied, cutting can be performed on the grasped tissue by mechanical friction force by the US energy and heat generation by the friction. Further, with a bipolar type handpiece that passes the HV signal applied to the distal end portion to the jaw which is a counter electrode, cutting can be performed for the grasped tissue without application of the US energy. However, the handpiece which grasps tissue by sandwiching the tissue cannot perform "treatment of making an incision line".

Note that as already described, the conventional HV apparatus can stop bleeding while cutting in the blend mode. However, this is for tissue or the like of a body surface that hardly bleeds, and sufficient stoppage of bleeding is not easy with organs having a large number of blood vessels therein such as a liver.

Further, with the monopolar type (monopole type) handpiece 2, a pressing force is not so strong as the grasping force by a bipolar type handpiece even if the treatment section 9 which performs ultrasound vibration is pressed against tissue. Therefore, heat generation by friction force and friction is small, and tissue cannot be cut mechanically or thermally. Further, the heat generation of the treatment section 9 to which only the HV signal (HV energy) of a coagulation waveform is applied is insufficient, and the treatment section 9 cannot transpire living tissue, and cannot make an incision line.

In contrast with this, in the surgical operation system 1, instead of the effect which is a simple combination of the effect obtained by application of only a high-frequency current and the effect obtained by application of only ultrasound vibration, an effect that is not less than the sum of the effects which are individually brought about by application of the high frequency current and application of ultrasound vibration, namely, a synergistic effect can be obtained. As a matter of course, it is extremely difficult to predict such a synergistic effect.

In order to obtain the above described synergistic effect in the surgical operation system 1, it is important that the HV signal has a coagulation waveform, first of all. As is already described, with only the HV signal of a coagulation waveform, living tissue cannot be transpired. However, as shown in FIG. 6, in the surgical operation system 1, the HV signal of a coagulation waveform is applied to the treatment section 9 together with the US signal, whereby bleeding can be stopped while an incision line is made on a liver in the pressing direction of the treatment section 9.

Figure 7A:
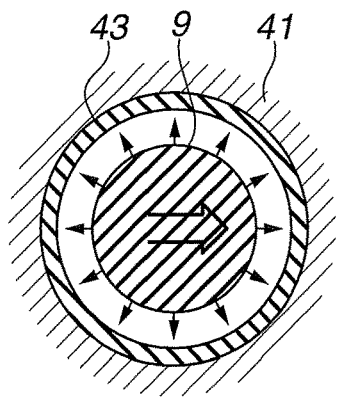
FIG. 7A is a schematic sectional view of a treatment section for explaining a treatment in a case of only HV energy being applied.

As shown in FIG. 7A, in a state in which ultrasound vibration is not applied, namely, in a state in which only the HV signal is applied, the HV signal of the coagulation waveform from the treatment section 9 isotropically flows to the surrounding tissue, even if the surgeon operates and presses the treatment section 9 in an intended direction of the organ 41. For example, many discharges by the HV signal occur not only to the pressing direction of the treatment section 9 but also to the direction orthogonal to the pressing direction, and the like. Therefore, as shown in FIG. 7A, large heat generation does not locally occur, and tissue 43 that is coagulated by thermal denaturation, and has high impedance with moisture vaporized is formed around the treatment section 9.

Figure 7B:
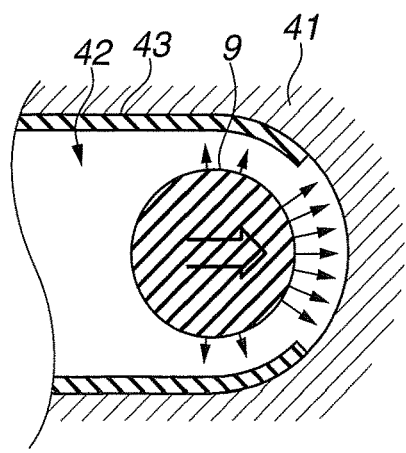
FIG. 7B is a schematic sectional view of the treatment section for explaining a treatment in a case of the HV energy and US energy being applied.

When the treatment section 9 which performs ultrasound vibration and has the HV signal applied thereto is operated and pressed in a predetermined direction, as shown in FIG. 7B, the HV signal with the coagulation waveform from the treatment section 9 intensively flows to the tissue in the pressing direction. In other words, discharges by the HV signal with the coagulation waveform concentrates into a space between the treatment section 9 and the tissue in the pressing direction. Namely, polarity occurs to the discharge by the HV signal. Therefore, even with the HV signal of the coagulation waveform, the pressed tissue is transpired by large heat generation, and the incision line 42 is made in the pressing direction.

When the treatment section 9 advances and moves in the cut tissue by pressing operation, a wall surface (cut surface) of the tissue located in the direction orthogonal to a traveling direction of the treatment section 9 has a long distance from the treatment section 9, and therefore, the HV signal does not concentrate on the wall surface so much as compared with the traveling direction. Therefore, the cut surface has a temperature suitable for coagulation, has moisture vaporized, and is increased in impedance. Therefore, whereas the tissue in the pressing direction of the treatment section 9, that is, in the traveling direction transpires, bleeding of the tissue of the cut surface which the treatment section 9 passes is stopped.

Note that the cause of occurrence of polarity in the discharge by the HV signal is conceivable as follows.

(A) The HV signal concentrates into a low impedance region of a parenchyma organ generated by the ultrasound vibration of the treatment section 9. Namely, when the treatment section 9 which performs ultrasound vibration and has the HV signal applied thereto is operated and pressed in a predetermined direction, only a region that is pressed of the parenchyma organ increased in impedance around the treatment section 9 is physically exfoliated by the ultrasound vibration. Thereby, the parenchyma organ with a high moisture content is exposed to a surface. In other words, by the effect of pushing a side incised organ by the ultrasound vibration, low impedance tissue appears in the pushing direction. Thereupon, the HV signal applied to the treatment section 9 locally concentrates into the low impedance tissue with a high moisture content. Therefore, polarity occurs to the discharge by the HV signal.

(B) The treatment section 9 is repeatedly brought into a contact state and a non-contact state with the tissue in the pressing direction in accordance with the ultrasound vibration. Namely, when the treatment section 9 which performs ultrasound vibration is operated and pressed, the distance between the treatment section 9 and the tissue in the pressing direction varies. Further, at the moment when the treatment section 9 comes to be not in contact with the tissue, an atmospheric pressure of a space between the treatment section 9 and the tissue becomes low. In contrast with this, at the moment when the treatment section 9 comes into contact with the tissue, the atmospheric pressure of the space between the treatment section 9 and the tissue becomes high. Namely, in response to the ultrasound vibration of the treatment section 9, the pressure of the space between the treatment section 9 and the tissue in the pressing direction varies. In this manner, the distance between the treatment section 9 and the parenchyma organ continues to vary in a range of, for example, 0 to 200 μm by the ultrasound vibration, and thereby, a state (distance, pressure) in which a discharge easily occurs is brought about during variation. Therefore, the HV signal which is applied to the treatment section 9 locally concentrates into the tissue in the pressing direction. Therefore, anisotropy occurs in the discharge direction.

(C) The HV signal concentrates along a path where particles formed from components (moisture and oil components, and moisture and oil mixture components) dispersed from a parenchyma organ due to ultrasound vibration are present. Namely, when the treatment section 9 which performs ultrasound vibration is operated and pressed, the tissue is crushed by the ultrasound vibration, is further atomized, and becomes particles to be suspended in a space. The moisture configuring the tissue becomes water vapor particles, and the oil components configuring the tissue becomes oil particles. The mixture particles including moisture and oil components are also generated. Therefore, in the space between the treatment section 9 and the tissue, the particles including the components dispersed from the tissue are unevenly distributed. Therefore, the HV signal concentrates along the path where the particles including the components which are dispersed from the tissue are present. Accordingly, polarity occurs to the discharge by the HV signal.

Note that in the surgical operation system of the present embodiment, if the HV signal which is applied simultaneously with the US signal has a coagulation waveform, the effect is provided, and 30 W to 70 W inclusive is especially preferable. With the aforementioned lower limit or more, an incision line can be made in the pressing direction by the HV signal concentrating into the electrode portion, and with the aforementioned upper limit or less, the tissue which the treatment section 9 passes is coagulated and bleeding can be stopped. Further, the crest factor CF of the coagulation waveform of the HV signal is preferably 5 or more, more preferably 5.5 or more, and especially preferably 6 or more. If the crest factor CF is the above described lower limit or more, an incision line can be made in the pressing direction by the HV signal concentrated in the electrode portion, and the tissue which the treatment section 9 passes is coagulated and bleeding can be stopped. Further, the upper limit value of the crest factor CF is not especially limited, but is preferably 10 or less, for example, from the specifications and the like of the HV apparatus.

The vibration speed of the ultrasound vibration of the treatment section 9 by the US signal is preferably 8 m/sec to 18 m/sec inclusive. Further, the amplitude of the ultrasound vibration of the treatment section 9 by the US signal is preferably larger than 0 μm and smaller than 200 μm. Note that when the frequency of the US signal is 47 kHz, at a vibration speed of 8 m/sec, the amplitude of the treatment section 9 is 60 μm, and at a vibration speed of 18 m/sec, the amplitude of the treatment section 9 is 120 μm.

Operation of the Surgical Operation System

Figure 8:
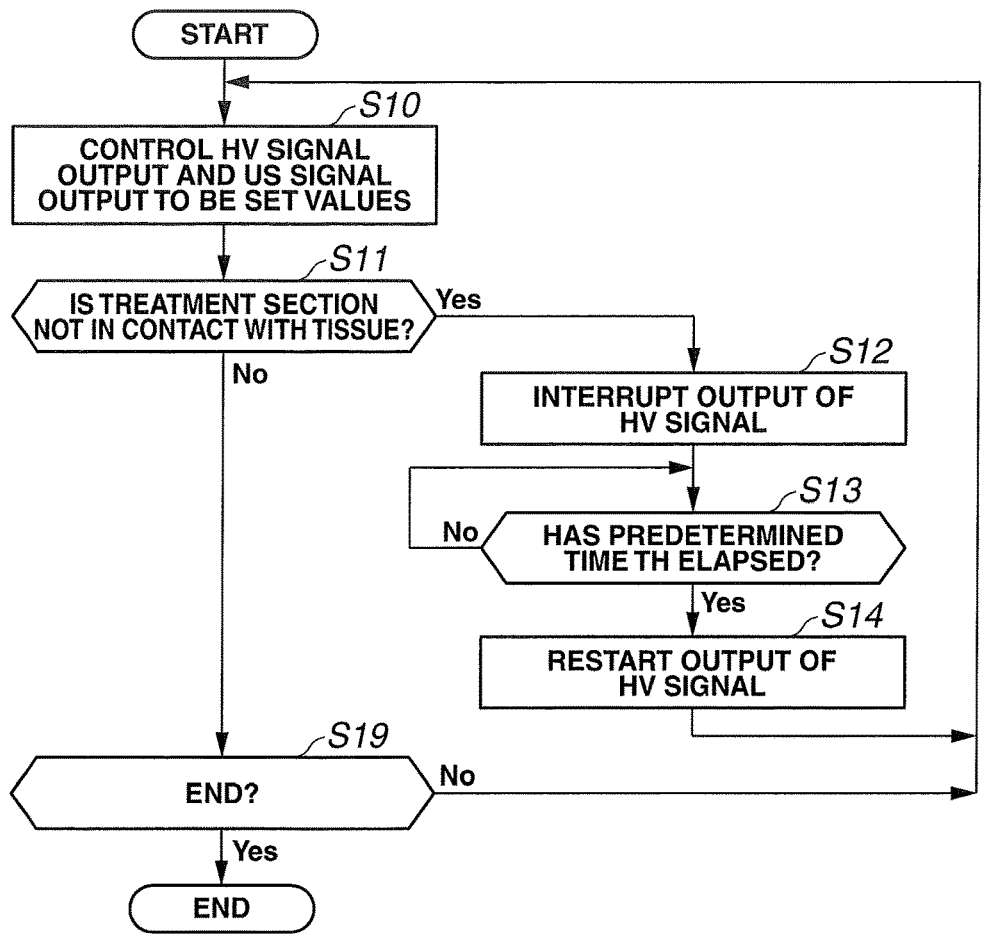
FIG. 8 is a flowchart for explaining a flow of processing of the surgical operation system of the first embodiment.

Next, with use of the flowchart of FIG. 8, an operation of the surgical operation system 1 will be described.

Step S10

When a treatment is started, the US signal main control section 51c performs feedback control of the US signal output section 50 so that the US signal output becomes the US signal output corresponding to a set value of the setting section 18a, based on the value detected by the US signal voltage detection section 52b of the US signal detection section 52. Further, the HV signal main control section 61c performs feedback control of the HV signal output section

60 so that the HV signal output becomes the HV signal output of the coagulation waveform corresponding to the set value of the setting section 19*a*, based on the value detected by the HV signal current detection section 62*a* of the HV signal detection section 62.

Step S11

When the HV signal auxiliary control section 51*b* senses that the treatment section 9 separates from the tissue based on a change value (differential value) of the impedance of the US signal, for example, which is detected by the US signal detection section 62 (S11; Yes), processing from step S12 is performed.

Step S12

The HV signal auxiliary control section 51*b* controls the HV signal relay 69 into an OFF state (open state). The time period from detection of the US signal until application of the HV signal to the treatment section 9 stops is 1 ms or less.

Here, the reason why it is sensed that the treatment section 9 separates from the tissue based on the US signal is that especially in the processing of the tissue having much fat where a high-energy discharge easily occurs, the change of the HV signal is small even when the treatment section 9 is in a non-contact state, as compared with the time of a contact state, but the change of the US signal is large. Namely, the tissue having much fat has a high electric resistance, and therefore, even in the non-contact state, a large change does not occur to the HV signal as compared with the time of the contact state. However, the US signal generates a large change when the non-contact state is brought about as compared with the time of the contact state, because the mechanical load significantly decreases.

Note that the US signal for sensing that the treatment section 9 separates from the tissue is not limited to the change value of the impedance of the US signal, but may be US signals detected by various configurations as will be described later.

Step S13

The HV signal auxiliary control section 51*b* keeps the OFF state of the HV signal relay 69 until a predetermined HV signal output wait time TH of, for example, 15 ms elapses (S13; No).

Step S14

After the predetermined HV signal output wait time TH elapses (S13; Yes), the HV signal auxiliary control section 51*b* controls the HV signal relay 69 to the ON state (continuity state). Namely, the HV signal auxiliary control section 51*b* controls the HV signal output section 60 to restart output of the HV signal which is stopped.

Subsequently, the process from S10 is repeated.

The treatment section 9 comes into the contact state with the tissue to perform the treatment again, even if the treatment section 9 temporarily separates from the tissue. In the surgical operation system 1, output of the HV signal is automatically restarted after the predetermined HV signal output wait time TH elapses, and therefore, favorable operability is provided. Note that the HV signal output wait time TH is preferably 5 ms to 50 ms, and especially preferably 10 ms to 20 ms. If the HV signal output wait time TH is within the above described range, a high-energy discharge does not occur, and no trouble occurs to the operation.

Step S19

Until the treatment is finished (S19; Yes), the processing from step S10 is repeatedly performed.

As in the above description, the surgical operation system 1 includes the exclusive HV signal auxiliary control section 51*b* for performing control that stops output of the HV signal at a high speed when the treatment section 9 separates from the tissue.

In particular, in a laparoscopic surgical operation which has increasingly become prevalent in recent years, the probe needs to be operated on tissue in an extremely limited movable range. The surgical operation system 1 can efficiently perform a treatment by the synergetic effect of ultrasound vibration and a high-frequency current, and includes the HV signal auxiliary control section 51*b* which controls the HV signal output section 60 based on the US signal and has a response time shorter than the HV signal main control section 61C, and therefore, suppresses occurrence of a high-energy discharge even if the treatment section 9 separates from the tissue.

Therefore, there is no fear of deterioration of the treatment section 9 being accelerated, and the treatment section 9 or the other treatment instruments and the like being damaged, due to occurrence of a high-energy discharge.

Namely, the surgical operation system 1 can perform bleeding stopping processing while making an incision line in the pressing direction, by simultaneously applying ultrasound vibration and a high-frequency current to the treatment section, has no fear of occurrence of a spark discharge (high-energy discharge) with large energy, and has favorable operability.

Next, configuration examples for use in high-speed control of the surgical operation system 1 of the embodiment will be described.

Configuration 1

The HV signal auxiliary control section 51*b* performs control based on an integrated value of the signals of a frequency band from the fundamental frequency to the frequency which is twice as high as the fundamental frequency, which are included in the US signal.

Figure 9:
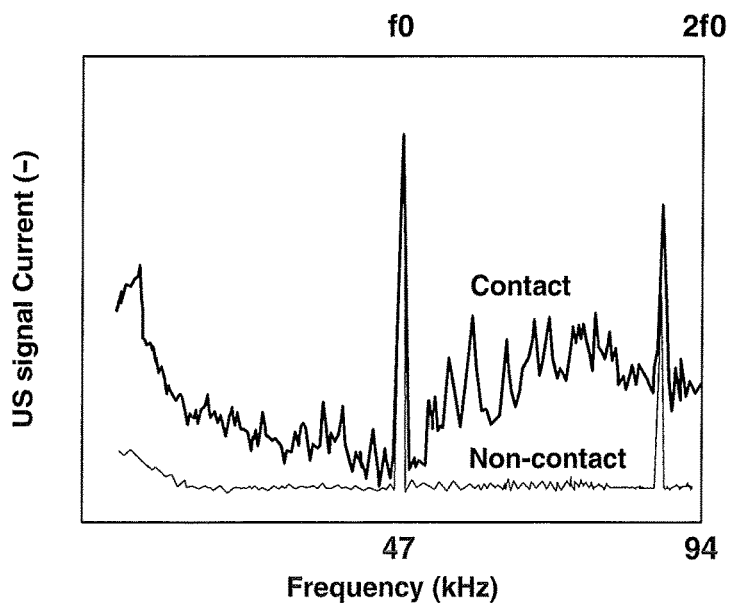
FIG. 9 is a frequency spectrum diagram for explaining signals of the surgical operation system of the first embodiment.

When the treatment section 9 is in contact with tissue, distortion occurs to the current waveform of the US signal. Namely, as shown in FIG. 9, at a contact time, a larger number of high-frequency components are included in the US signal of a sine wave of a fundamental frequency (f0) that is a resonance frequency, as compared with a non-contact time.

Therefore, in particular, the intensities of the signals of the frequency band from the fundamental frequency (f0) to a frequency (2f0) which is twice as high as the fundamental frequency are compared with the intensities at the time of a contact state, and thereby, it can be determined that the treatment section 9 separates from the tissue.

The intensities of the signals of the frequency band (f0 to 2f0) from the fundamental frequency (f0) to the frequency (2f0) which is twice as high as the fundamental frequency are extracted from the US signal with use of, for example, a band-pass filter.

Further, the HV signal auxiliary control section 51*b* more preferably performs control based on the change speed of the signal intensity of the frequency band (f0 to 2f0), that is, the differential value, because higher-speed control is enabled.

Configuration 2

The HV signal auxiliary control section 51b performs control based on the signals of the frequencies which are odd multiples of the fundamental frequency, which are included in the US signal.

Figure 10A:
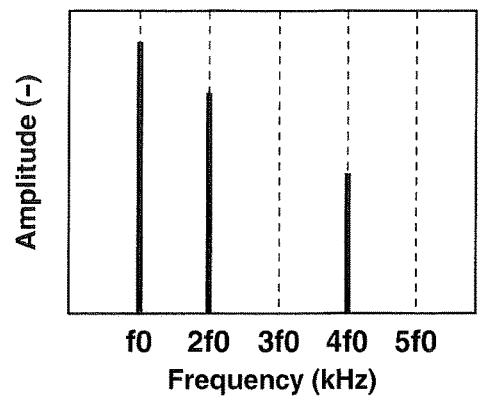
FIG. 10A is a frequency spectrum diagram for explaining the signal of the surgical operation system of the first embodiment.
Figure 10B:
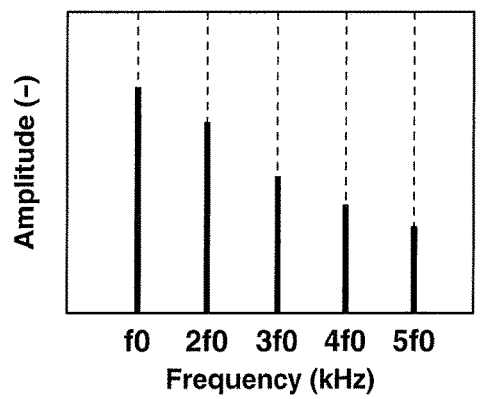
FIG. 10B is a frequency spectrum diagram for explaining the signal of the surgical operation system of the first embodiment.

As is already described, when the treatment section 9 is in contact with tissue, distortion occurs to the current waveform of the US signal. As a result, as compared with the amplitude of the US signal at the time of a non-contact state as shown in FIG. 10A, the amplitude of the US signal at the time of a contact state shown in FIG. 10B increases especially in the frequencies (3f0, 5f0 , , , ) which are odd multiples of the fundamental frequency (f0).

The amplitudes of the signal of a frequency (3f0) that is three times as high as the fundamental frequency (f0) and the US signal of a frequency (5f0) that is five times as high as the fundamental frequency (f0) are extracted from the US signal by a band-pass filter. From the viewpoint of the intensities of the signals which can be extracted and the circuit mounting cost, signals of (3f0 and 5f0) are preferably extracted, but only the signal of (3f0) may be extracted, or the signals of (3f0, 5f0, 7 f0, . . . ) and the like may be extracted.

Further, the HV signal auxiliary control section 51b more preferably perform control based on the change speed, namely, the differential value of the extracted signals, because higher-speed control is enabled.

Configuration 3

The HV signal auxiliary control section 51b performs control based on the phase difference between the voltage and the current of the US signal.

Figure 11:
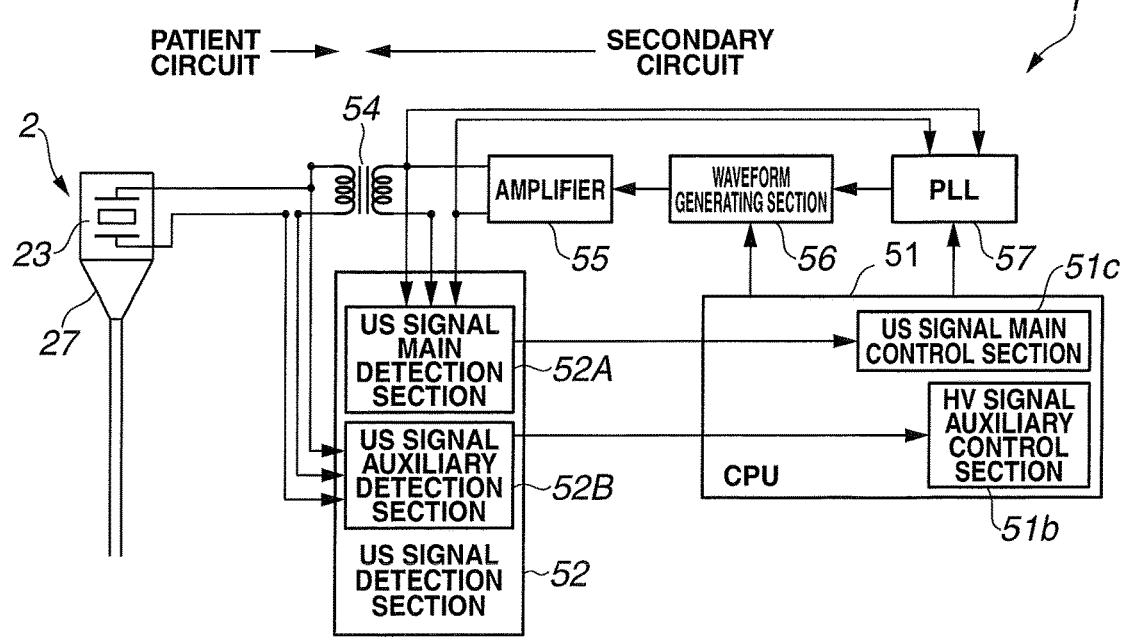
FIG. 11 is a configuration diagram for explaining a configuration example of the surgical operation system of the first embodiment.
Figure 12:
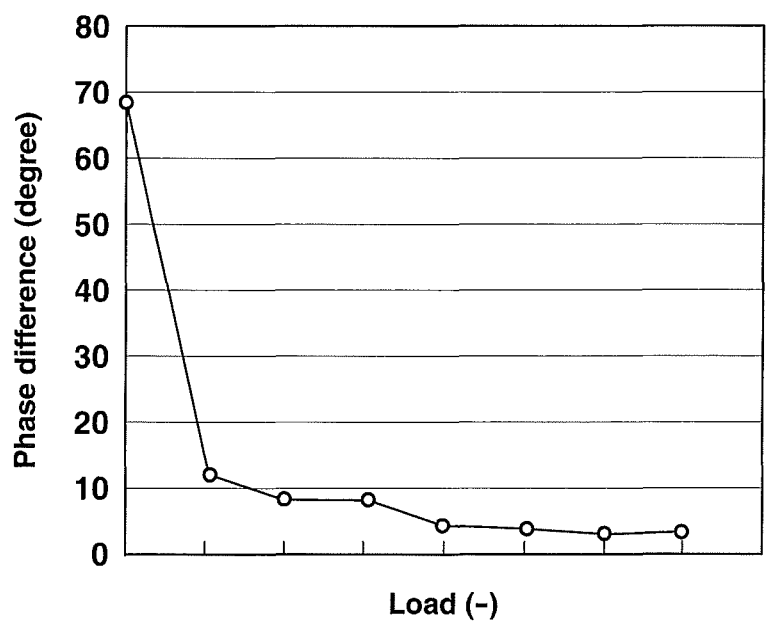
FIG. 12 is a graph showing one example of an influence that application of a load to the treatment section exerts on a phase difference of a current and a voltage, in the surgical operation system of the first embodiment.

The US signal of the US apparatus 5 is subjected to PLL control in the PLL section 57 of a secondary circuit via the output transformer 54 as shown in FIG. 11. Note that FIG. 11 shows only some of the components of the surgical operation system. Here, the output transformer 54 which provides insulation between a patient circuit and the secondary circuit is designed to be able to drive for a long period of time with the maximum current and the maximum voltage. Therefore, in the patient circuit without the PLL section 57, the voltage of the US signal is a voltage much lower than the maximum voltage, when the treatment section 9 is not in contact with tissue, namely, when the mechanical load (load) is small. As shown in FIG. 12, when the load is small, the phase difference between the voltage and the current of the US signal is large.

As shown in FIG. 11, by the US signal detection section 52 having the US signal auxiliary detection section 52B which detects the US signal of the patient circuit, in addition to the US signal main detection section 52A which detects the US signal of the secondary circuit, it can be sensed that the treatment section 9 is brought into a non-contact state with tissue, from the phase difference of the current and the voltage of the US signal of the patient circuit.

Further, the HV signal auxiliary control section 51b more preferably performs control based on the change speed of the detected signal, namely, the differential value, because higher-speed control is enabled.

Configuration 4

The HV signal auxiliary control section 51b performs control based on the change speed of the resonance frequency of the US transducer.

The fundamental frequency of the US signal of the US apparatus 5 is changed by the PLL section 27 in response to change of the resonance frequency of the US transducer. The resonance frequency changes in response to contact/non-contact of the treatment section 9 with tissue, that is, the mechanical load of the treatment section 9. Here, the resonance frequency also changes in accordance with a temperature. Therefore, the US signal auxiliary detection section 52B detects the change speed (differential value) of the resonance frequency, and the HV signal auxiliary control section 51b senses that the treatment section 9 is brought into a non-contact state with the tissue by occurrence of abrupt change of a predetermined value or more of the change speed.

Note that the configurations which can be used in the surgical operation system 1 are not limited to the configurations described above, and various configurations having similar effects can be used. Further, two or more of the configurations may be used in combination. For example, the configuration 1 and the configuration 2 are used, and when the level of the US signal of at least any one of the configurations becomes a predetermined value or more, the HV signal auxiliary control section 51b may stop output of the HV signal.

Modification of the First Embodiment

Figure 13:
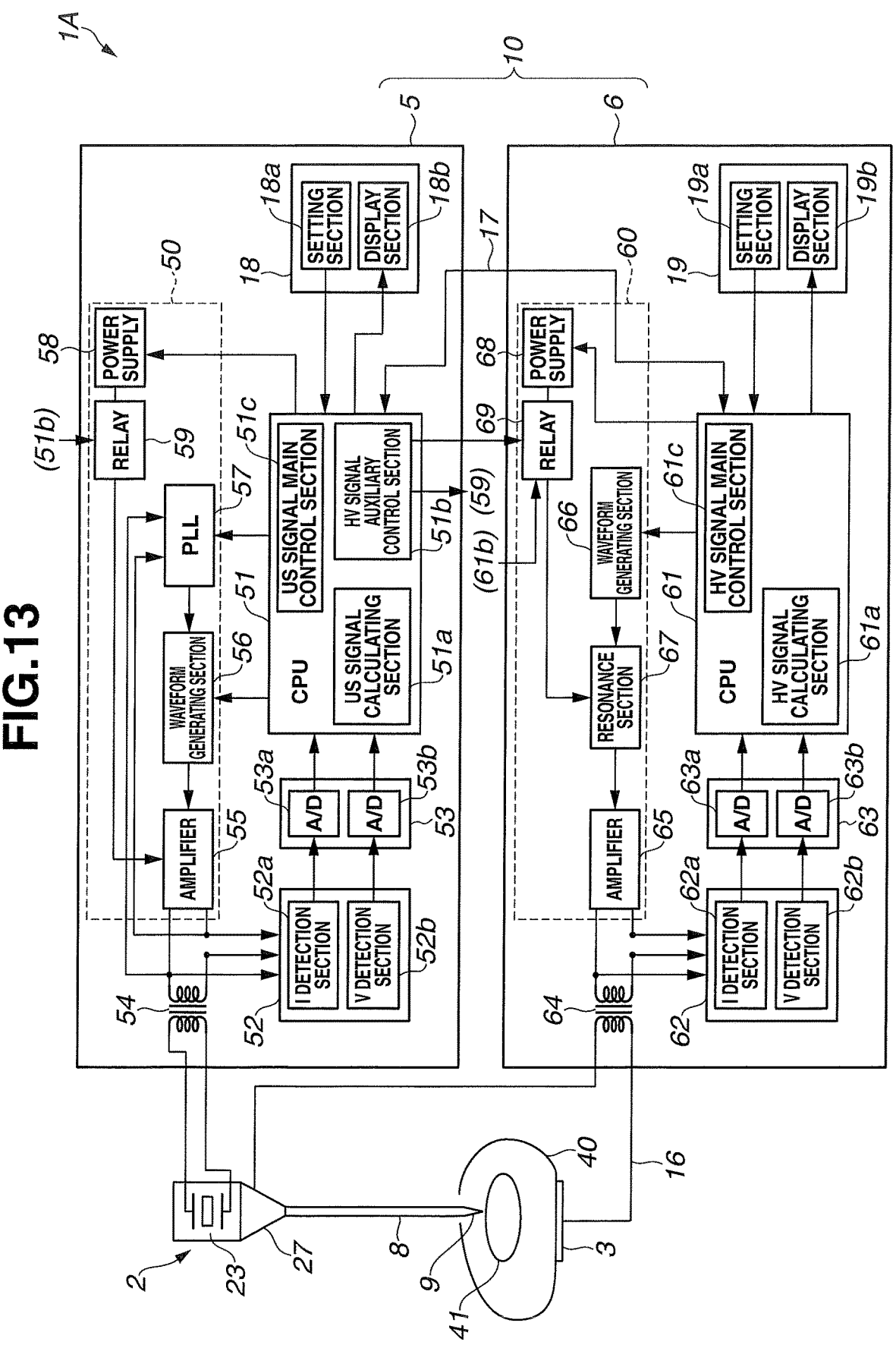
FIG. 13 is a configuration diagram showing a configuration of a surgical operation system of a modification of the first embodiment.

Next, a surgical operation system 1A of a modification of the first embodiment will be described. Since the surgical operation system 1A of the present modification is analogous to the surgical operation system 1 of the first embodiment as shown in FIG. 13, the components with the same functions are assigned with the same reference signs, and the description thereof will be omitted.

The HV signal auxiliary control section 51b of the surgical operation system 1A also performs control of stopping output of the US signal simultaneously with control of stopping output of the HV signal, when the treatment section 9 separates from tissue.

In the US signal output section 50, a US signal relay 59 that is a switch that turns on/off output of a signal received from the power supply 58 to a post-stage circuit is placed. Namely, the US signal relay 59 outputs the signal to the post-stage circuit in an ON state (continuity state), but does not output the signal to the post-stage circuit in an OFF state (open state).

The HV signal auxiliary control section 51b controls not only the HV signal relay 69, but also the US signal relay 59. The surgical operation system 1A has the effect which the surgical operation system 1 has, and further can more reliably prevent occurrence of a high-energy discharge. Namely, the surgical operation system 1A is more favorable in operability than the surgical operation system 1.

Note that the HV signal auxiliary control section 51b preferably controls the US signal output section 50 to restart the output of the US signal which is stopped after a predetermined US signal output wait time period, in the same manner as the HV signal auxiliary control section 51b controls the HV signal output section 60 to restart the output of the HV signal which is stopped after the predetermined HV signal output wait time period.

Second embodiment

Next, a surgical operation system 101 of a modification of a second embodiment will be described. Since the surgical operation system 101 is analogous to the surgical operation system 1 of the first embodiment, the components with the same functions are assigned with the same reference signs, and the description thereof will be omitted.

Figure 14:
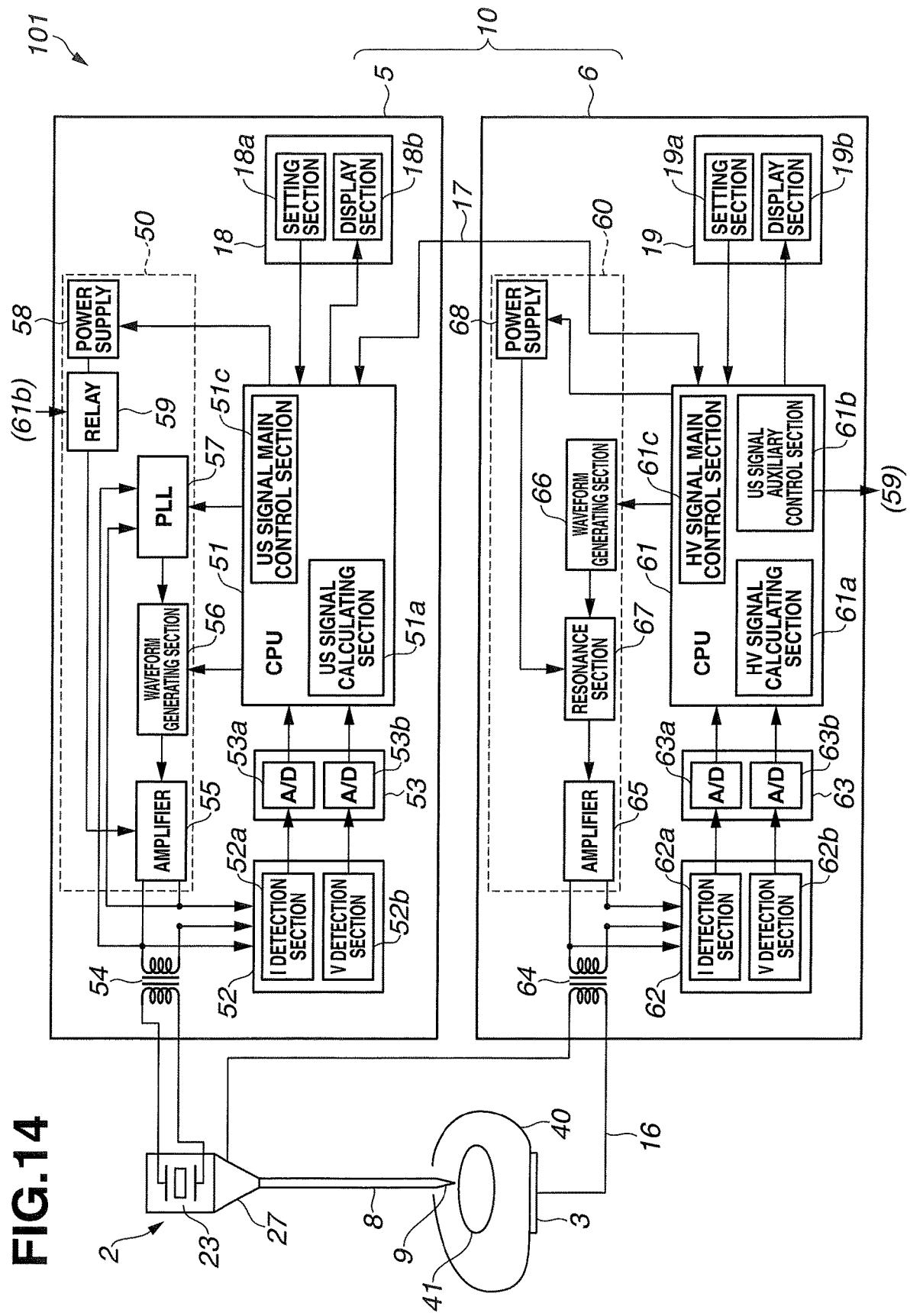
FIG. 14 is a configuration diagram showing a configuration of a surgical operation system of a second embodiment.

With use of FIG. 14, a configuration of the surgical operation system 101 will be described. As in the following description, the surgical operation system 101 includes a US signal auxiliary control section 61b that controls the US signal output section 50 based on an HV signal, and has a response time shorter than the US signal main control section 51c.

The US apparatus 5 which generates a US signal and supplies ultrasound (US) energy to the treatment section 9 has the central processing unit (CPU) 51, the US signal detection section 52, the A/D conversion section 53, the output transformer 54, the amplifier 55, the waveform generating section 56, the PLL section 57, the power supply 58 and the drive signal relay (US signal relay) 59. The output transformer 54, the amplifier 55, the waveform generating section 56, the PLL section 57, the power supply 58 and the US signal relay 59 configure the drive signal output section (US signal output section) 50. The US signal is an AC signal of a sign wave of a predetermined fundamental frequency (resonance frequency), for example.

The US signal relay 59 is an ON/OFF switch which shuts off output of the signal received from the power supply 58 to the post-stage circuit. Namely, the US signal relay 59 outputs the signal to the post-stage circuit in an ON state (continuity state), but does not output the signal to the post-stage circuit in an OFF state (open state).

The CPU 61 which performs control of the entire HV apparatus 6 and control of the US signal relay 59 has the high-frequency signal calculating section (HV signal calculating section) 61a, the drive signal auxiliary control section (US signal auxiliary control section) 61b and the high-frequency signal main control section (HV signal main control section) 61c. Note that the HV signal calculating section 61a, the US signal auxiliary control section 61b and the HV signal main control section 61c may be respectively configured by different CPUs. Further, the CPU 61 may be the same CPU as the CPU 51.

Feedback control that is ordinary control performed by the US signal main control section 61c and the HV signal main control section 51c is control for keeping, for example, a signal intensity at a predetermined intensity. In contrast with this, the US signal auxiliary control section 61b controls the US signal relay 59 of the US signal output section 50 to an ON state or an OFF state, based on the HV signal detected by the HV signal detection section 62. Namely, the control which is performed by the US signal auxiliary control section 61b is ON/OFF control that only stops output of a signal, and therefore, can relatively easily realize high-speed control with a short response time, as compared with the ordinary control that increases and decreases output.

As already described, the treatment by the handpiece in which ultrasound vibration and a high-frequency current are simultaneously applied to the treatment section has the fear of occurrence of a spark discharge (hereinafter, called "high-energy discharge") with large energy, which hardly occurs in the treatment by the handpiece in which only a high-frequency current is applied to the treatment section.

For example, there is the fear that when the treatment section 9 comes in contact with another treatment instrument made of a metal or the like, a high-energy discharge occurs, and the treatment section 9, the other treatment instrument or the like is damaged.

In the surgical operation system 101, when the US signal auxiliary control section 61b senses that the treatment section 9 comes in contact with another treatment instrument made of a metal, or the like based on the HV signal detected by the HV signal detection section 62, the US signal auxiliary control section 61b controls the US signal relay 59 of the US signal output section 50 to an OFF state. Namely, after an extremely short time from detection of the HV signal, the ultrasound vibration of the treatment section 9 stops. Therefore, even if the treatment section 9 contacts another treatment instrument, a high-energy discharge does not occur.

It is conceivable that immediately before a high-energy discharge occurs, a discharge that has a small intensity, but differs from an ordinary discharge occurs as a precursory phenomenon thereof. The US signal auxiliary control section 61b stops output before a high-energy discharge occurs based on the signal change due to the precursory phenomenon or the like, and thereby prevents occurrence of the high-energy discharge.

Namely, in a strict sense, "when the treatment section 9 contacts the metallic instruments" does not mean "when the treatment section 9 completely contacts", but rather means "when the treatment section 9 starts to contact".

In addition, the US signal auxiliary control section 61b has a response time shorter than the US signal main control section 61c. Namely, response times of the US signal main control section Mc and the HV signal main control section 61c which perform feedback control are preferably 5 ms (milliseconds) or longer, and, for example, 100 ms.

In contrast with this, the response time of the US signal auxiliary control section 61b is preferably 1 ms or shorter, and, for example, 0.5 ms. Further, the US signal relay 59 is also a circuit of a simple operation that is an ON/Off operation, and therefore, a response time thereof is 1 ms or shorter, and is, for example, 0.2 ms. The US signal relay 59 may be a mechanical type switch, or a semiconductor switch.

Note that if the response time is 1 ms or less, an attenuation section that reduces signal output to substantially zero, namely, reduces a signal intensity to such an intensity that does not influence a treatment or the like may be used, in place of the relay type ON/OFF switch. For example, when the amplifier 55 can be controlled at a high speed, the function of the attenuation section may be realized by control of the amplifier 55. Namely, in the following description and the like, "stops signal output" is the concept also including the case of "reducing signal output to substantially zero".

Note that the HV signal detection section 62 detects signals at intervals of 1 ms or less. The US signal main control section 51c processes the signals which the US signal detection section 52 detects at intervals of 100 ms, for example.

The US signal auxiliary control section 61b sequentially processes the signals which the HV signal detection section 62 detects at intervals of 1 ms or less, but the HV signal main control section 61c processes the signals which the HV signal detection section 62 detects at predetermined intervals longer than the detection intervals of the HV signal detection section 62, for example, at intervals of 100 ms. The HV signal main control section 61c may perform control with use of an integrated value or a mean value of the signals which the HV signal detection section 62 detects at intervals of 1 ms or less.

Note that as shown in FIG. 5, the HV signal detection section 62 may have an HV signal main detection section 62A and an HV signal auxiliary detection section 62B. Further, the HV signals detected by the HV signal main detection section 62A and the HV signals detected by the HV signal auxiliary detection section 62B may be sampled from the same spot on the circuit, or may be sampled from different spots.

The HV signal auxiliary detection section 62B has the detection intervals shorter than the HV signal main detection section 62A. For example, the HV signal main detection section 62A detects signals at intervals of 5 ms or more, for example, intervals of 100 ms, whereas the HV signal auxiliary detection section 62B detects signals at intervals of 1 ms or less, for example, intervals of 0.5 ms.

Subsequently, the HV signal main control section 61c performs ordinary feedback control based on the signals detected by the HV signal main detection section 62A. Further, the US signal main control section 51c performs ordinary feedback control based on the signals which the US signal main detection section 52A detects, and the US signal auxiliary control section 61b performs high-speed control with a high response speed based on the signals which the HV signal auxiliary detection section 62B detects.

The US signal main control section 51c and the HV signal main control section 61c can stably perform control if a loop processing time period of detection/response is in the aforementioned range or more. Namely, if the detection interval and the response time are too short in control of feedback, signal output is sometimes excessively increased in response to a noise signal which appears in a pulse form, for example. Therefore, the signal detection intervals and the response times of the US signal main control section 51c and the HV signal main control section 61c are preferably in the aforementioned range or more.

In contrast with this, the US signal auxiliary control section 61b needs to stop output of the HV signal, before a high-energy discharge occurs, when the treatment section 9 separates from tissue.

Therefore, the time period from detection of an HV signal until an operation of the US signal relay 59 is completed by control of the US signal auxiliary control section 61b is preferably 1 ms or less.

If the time period is the above described time period or less, occurrence of a high-energy discharge can be reliably prevented.

Note that the above described detection intervals, the above described response time and the time period until completion of the operation are preferably short, but in the industrially available systems, approximately 1 μs (microsecond) is a lower limit value.

Operation of the Surgical Operation System

Figure 15:
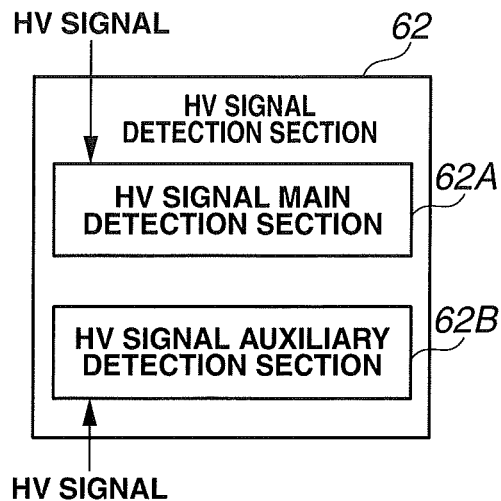
FIG. 15 is a configuration diagram showing a configuration of a signal detection section of the surgical operation system of the second embodiment.

Next, with use of a flowchart of FIG. 15, an operation of the surgical operation system 101 will be described.

Step S110

Step S110 is the same as step S10 of FIG. 7.

Step S115

When the US signal auxiliary control section 61b senses that that the treatment section 9 contacts a metallic instrument based on, for example, a differential value of the current of the HV signal (S115; Yes), processing from step S116 is performed.

Step S116

The US signal auxiliary control section 61b stops the HV signal in 1 ms or less from the HV signal detection.

The US signal auxiliary control section 61b controls the US signal relay 59 to an OFF state (open state). The time period from the detection of the HV signal until stop of application of the US signal to the ultrasound transducer 23 is 1 ms or less.

Here, the reason why it is sensed that the treatment section 9 contacts another treatment instrument made of a metal, or the like based on the HV signal is that the change of the HV signal is larger than the change of the US signal.

Note that the signal for sensing that the treatment section 9 contacts a metallic instrument is not limited to the differential value of the current of the HV signal detected in the HV signal detection section 62, but may be HV signals detected by various configurations, as will be described later.

Step S117

The US signal auxiliary control section 61b keeps the OFF state of the US signal relay 59 until a predetermined US signal output wait time TU of, for example, 150 ms elapses (S117; No).

Step S118

After the predetermined US signal output wait time TU elapses (S117; Yes), the US signal auxiliary control section 61b controls the US signal relay 59 to the ON state (continuity state). Namely, the US signal auxiliary control section 61b controls the US signal output section 50 to restart output of the US signal which is stopped.

Subsequently, the processing from S110 is repeated.

It is only for a short time that the treatment section 9 erroneously contacts the other treatment instrument made of a metal, or the like. In the surgical operation system 101, output of the US signal is automatically restarted after the predetermined US signal output wait time TH elapses, and therefore, favorable operability is provided. Note that the US signal output wait time TU is preferably 50 ms to 500 ms, and especially preferably 100 ms to 200 ms. If the US signal output wait time TU is within the above described range, a high-energy discharge does not occur, and no trouble occurs to the operation.

Step S119

Until the treatment is finished (S119; Yes), the processing from step S110 is repeatedly performed.

As in the above description, the surgical operation system 101 includes the exclusive US signal auxiliary control section 61b for performing control that stops output of the US signal at a high speed when the treatment section 9 contacts a metallic instrument.

In particular, in a laparoscopic surgical operation which has increasingly become prevalent in recent years, the probe needs to be operated on tissue that is held by a metallic forceps and a metallic clip in an extremely limited movable range. The surgical operation system 101 can efficiently perform a treatment by the synergetic effect of ultrasound vibration and a high-frequency current, and suppresses occurrence of a high-energy discharge even if the treatment section 9 contacts a metallic instrument.

Therefore, there is no fear that deterioration of the treatment section 9 is accelerated, and the treatment section 9, another treatment instrument or the like is damaged, due to occurrence of a high-energy discharge. Therefore, the surgical operation system 101 has favorable operability.

Next, configuration examples for use in high-speed control of the surgical operation system 101 of the embodiment will be described.

Configuration 1

The US signal auxiliary control section 61b performs control based on the signals of frequencies higher than the fundamental frequency, which are included in the HV signal.

When the treatment section 9 contacts a metallic instrument, the resistance becomes small, and therefore, a large current flows as the HV signal. Even before the treatment section 9 completely contacts the metallic instrument, a very weak discharge occurs to the metallic instrument from the treatment section 9. Thereupon, in the current of the HV signal including a sine wave of a predetermined fundamental frequency, for example, 350 kHz, the signals of frequencies higher than the fundamental frequency starts to be generated. In other words, the signals of the frequencies higher than the fundamental frequency are included in the HV signal.

Therefore, it can be sensed that the treatment section 9 starts to contact the metallic instrument by comparing the intensities of the signals of the frequencies higher than the fundamental frequency, which are included in the HV signal, with a predetermined value.

Further, the US signal auxiliary control section 61b more preferably performs control based on the change speed of the intensities of the detected signals, namely, a differential value, because control at a higher speed is enabled.

Configuration 2

The US signal auxiliary control section 61b performs control based on the change speed of the root means square value of the HV signal.

When the treatment section 9 starts to contact a metallic instrument, the current value (root means square value) of the HV signal starts to increase abruptly. When the current value of the HV signal increases to a predetermined value or more, a high energy discharge occurs. The US signal auxiliary control section 61b can stop the US signal before a high-energy discharge occurs, by performing control based on the change speed of the current value (root means square value) of the HV signal, namely, the differential value.

Configuration 3

The US signal auxiliary control section 61b performs control based on the distortion component of the HV signal.

When the treatment section 9 contacts a metal instrument, the resistance becomes small in the HV signal, and therefore, a large current flows. Thereupon, a distortion occurs to the current waveform of the HV signal of a predetermined fundamental frequency. The distortion of the HV signal is detected, and thereby start of contact can be sensed.

Note that the magnitude of a distortion increases with increase of specific resistance of a matter that the treatment section 9 contacts. For example, when the treatment section 9 contacts fat tissue, a distortion also occurs, but the magnitude of the distortion is smaller than when the treatment section 9 contacts lean meat tissue. Further, the magnitude of the distortion at the time of the treatment section 9 contacting a metallic instrument is much larger than when the treatment section 9 contacts lean meat tissue. Therefore, the present configuration is unlikely to cause an erroneous operation.

Note that the configurations that can be used in the surgical operation system 101 are not limited to the configurations described above, and various configurations that have similar effects can be used. Further, two or more configurations may be used in combination.

Modification 1 of the Second Embodiment

Figure 16:
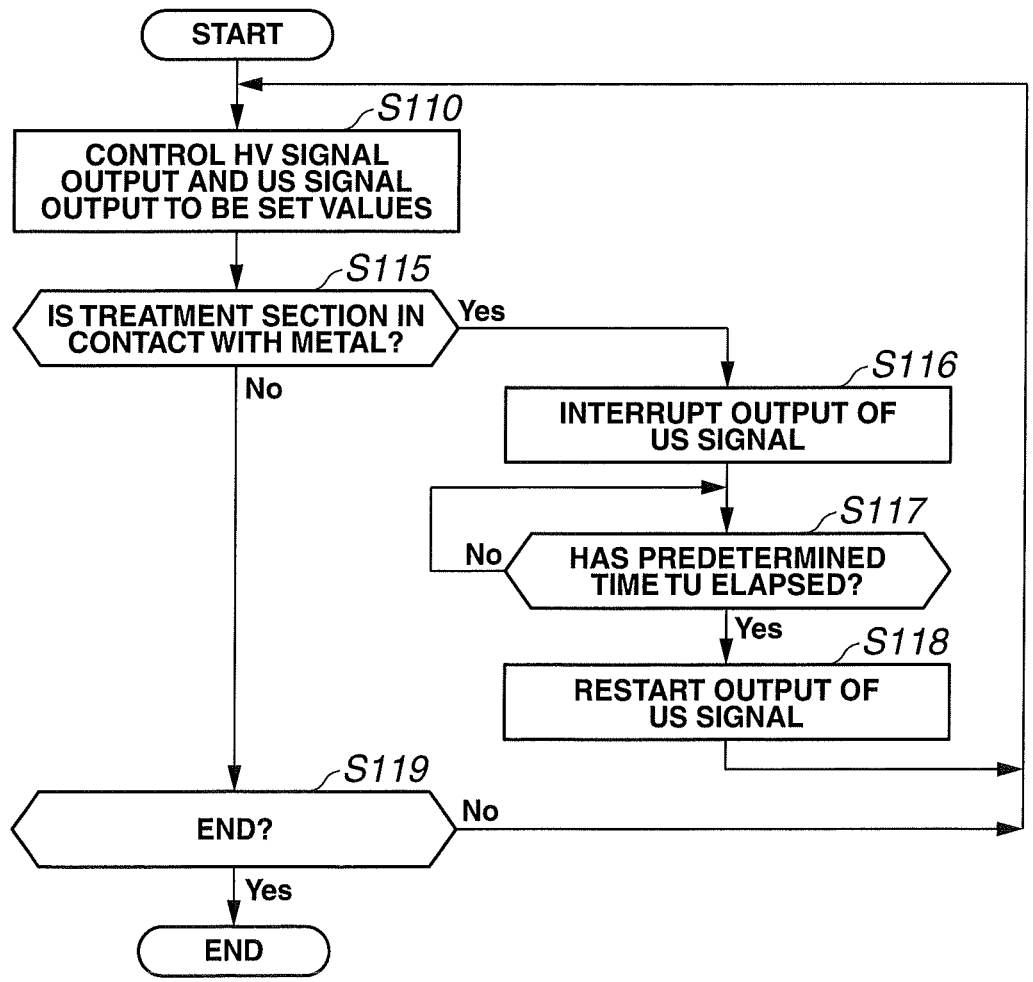
FIG. 16 is a flowchart for explaining a flow of processing of the surgical operation system of the second embodiment.

Next, a surgical operation system 101A of a modification 1 of the second embodiment will be described. Since the surgical operation system 101A of the present modification is analogous to the surgical operation system 101 of the second embodiment as shown in FIG. 16, the components with the same functions are assigned with the same reference signs, and the description thereof will be omitted.

The US signal auxiliary control section 61b of the surgical operation system 101A also performs control of stopping output of the HV signal simultaneously with control of stopping output of the US signal, when the treatment section 9 contacts another instrument made of a metal.

In the HV signal output section 60, an HV signal relay 69 that is an On/Off switch that shuts off output of a signal received from the power supply 68 to a post-stage circuit is placed. Namely, the HV signal relay 69 outputs the signal to the post-stage circuit in an ON state (continuity state), but does not output the signal to the post-stage circuit in an OFF state (open state).

The US signal auxiliary control section 61b controls not only the US signal relay 59, but also the HV signal relay 69.

The surgical operation system 101A has the effect which the surgical operation system 101 has, and further can more reliably prevent occurrence of a high-energy discharge. Namely, the surgical operation system 101A is more favorable in operability than the surgical operation system 101.

Note that the US signal auxiliary control section 61b preferably controls the HV signal output section 60 to restart output of the HV signal which is stopped after a predetermined HV signal output wait time period, in the same manner as the US signal auxiliary control section 61b controls the US signal output section 50 to restart output of the US signal which is stopped, after the predetermined US signal output wait time period.

Third Embodiment

Next, a surgical operation system 201 of a modification of a third embodiment will be described. Since the surgical operation system 201 is analogous to the surgical operation system 1 of the first embodiment and the surgical operation system 101 of the second embodiment, the components with the same functions are assigned with the same reference signs, and the description thereof will be omitted.

Configuration of the Surgical Operation System

Next, a configuration of the surgical operation system 201 will be described.

Figure 17:
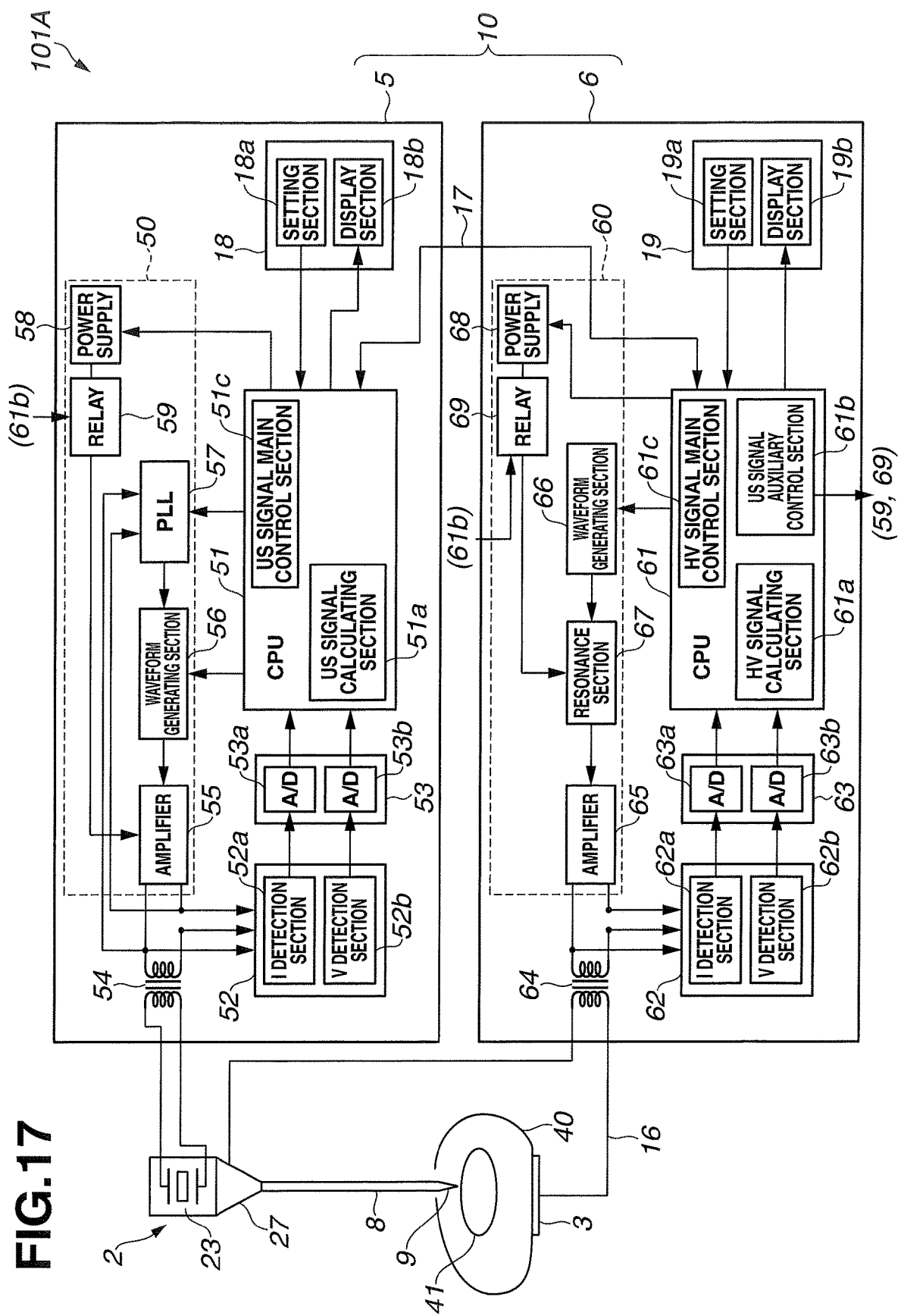
FIG. 17 is a configuration diagram showing a configuration of a surgical operation system of a modification of the second embodiment.

As shown in FIG. 17, the surgical operation system 201 has the configuration of the surgical operation system 1 and the configuration of the surgical operation system 101.

Namely, the surgical operation system 201 includes the US signal auxiliary control section 61b which controls the US signal output section 50 based on the HV signal, and has the response time shorter than the US signal main control section 51c, and the HV signal auxiliary control section 51b which controls the HV signal output section 60 based on the US signal, and has the response time shorter than the HV signal main control section 61C.

Operation of the Surgical Operation System

Figure 18:
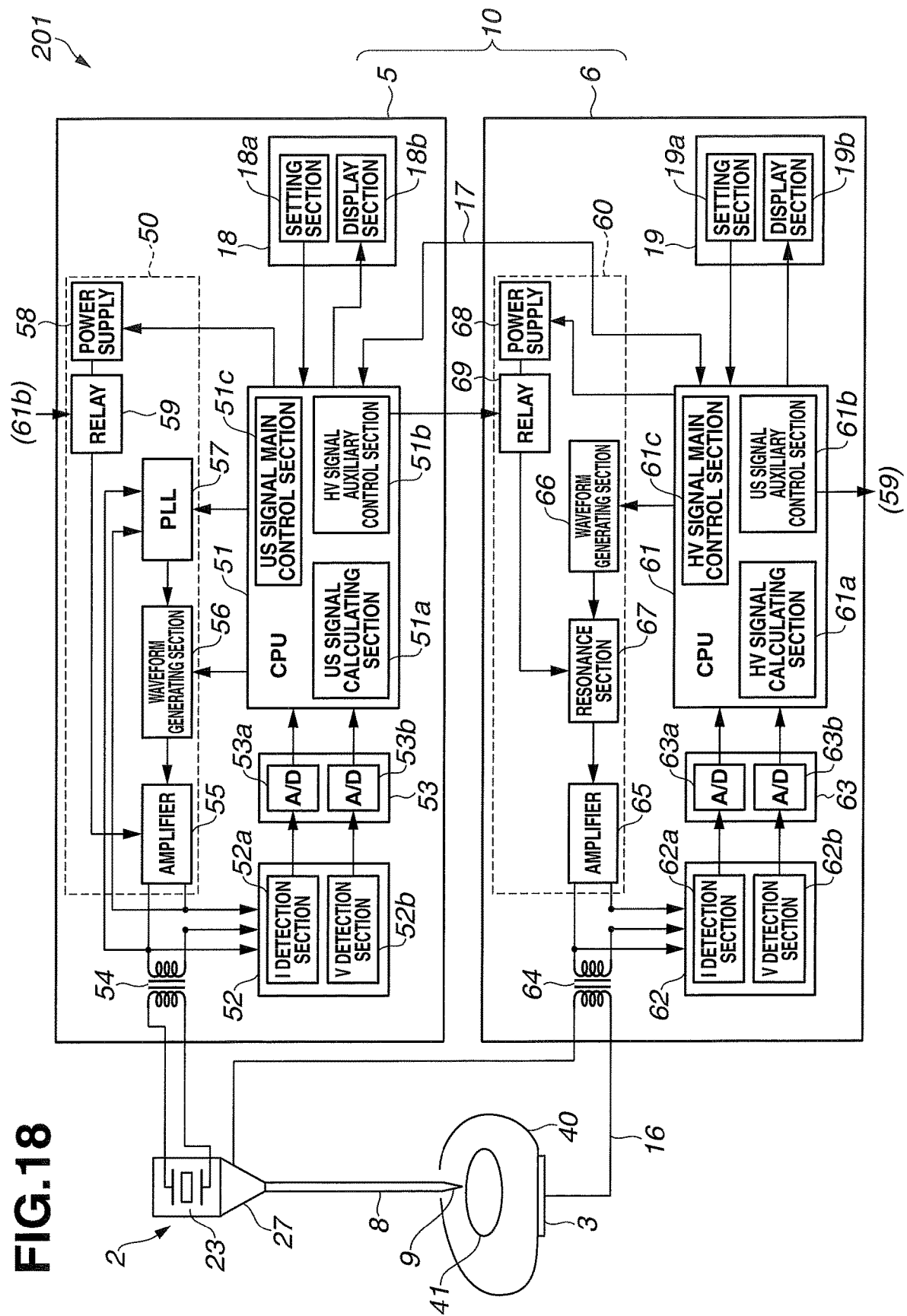
FIG. 18 is a configuration diagram showing a configuration of a surgical operation system of a third embodiment.

Next, with use of a flowchart of FIG. 18, an operation of the surgical operation system 201 will be described.

Step S210

When a treatment is started, the US signal main control section 51c performs feedback control of the US signal output section 50 so that the US signal output becomes the US signal output corresponding to a set value of the setting section 18a, based on the value detected by the US signal voltage detection section 52b of the US signal detection section 52. Further, the HV signal main control section 61c performs feedback control of the HV signal output section 60 so that the HV signal output becomes the HV signal output of the coagulation waveform corresponding to a set value of the setting section 19a,based on the value detected by the HV signal current detection section 62a of the HV signal detection section 62.

Note that when the treatment section 9 is in a non-contact state with the organ such as a liver that is a parenchyma organ for which the treatment section 9 performs treatment of "making an incision line", at the time of start of use, output of the HV signal is immediately stopped by the processing from step S11 which will be described later.

Step S211

When the HV signal auxiliary control section 51b senses that the treatment section 9 separates from the tissue based on a change value (differential value) of the impedance of the US signal, for example, which is detected by the US signal detection section 62 (S211; Yes), processing from step S212 is performed.

Step 212

The HV signal auxiliary control section 51b controls the HV signal relay 69 to an OFF state (open state). The time period from detection of the US signal until application of the HV signal to the treatment section 9 stops is 1 ms or less.

Here, the reason why it is sensed that the treatment section 9 separates from the tissue based on the US signal is that in the processing of the tissue having much fat where a high-energy discharge especially easily occurs, the change of the HV signal is small even when the treatment section 9 is in a non-contact state, as compared with when the treatment section 9 is in a contact state, but the change of the US signal is large. Namely, the tissue having much fat has a high electric resistance, and therefore, even in the non-contact state, a large change does not occur to the HV signal as compared with the time of the contact state. However, when the non-contact state is brought about, the mechanical load of the US signal significantly decreases, and therefore, as compared with the time of the contact state, the US signal generates a large change.

Note that the US signal for sensing that the treatment section 9 separates from the tissue is not limited to the change value of the impedance of the US signal, but may be US signals that are detected by various configurations as will be described later.

Step S213

The HV signal auxiliary control section 51b keeps the OFF state of the HV signal relay 69 until a predetermined HV signal output wait time TH of, for example, 15 ms elapses (S213; No).

Step S214

After the predetermined HV signal output wait time TH elapses (S213; Yes), the HV signal auxiliary control section 51b controls the HV signal relay 69 to the ON state (continuity state). Namely, the HV signal auxiliary control section 51b controls the HV signal output section 60 to restart output of the HV signal which is stopped.

Subsequently, the processing from S210 is repeated.

The treatment section 9 comes into the contact state with the tissue to perform the treatment again, even if the treatment section 9 temporarily separates from the tissue. In the surgical operation system 201, output of the HV signal is automatically restarted after the predetermined HV signal output wait time TH elapses, and therefore, favorable operability is provided. Note that the HV signal output wait time TH is preferably 5 ms to 50 ms, and especially preferably 10 ms to 20 ms. If the HV signal output wait time TH is within the above described range, a high-energy discharge does not occur, and no trouble occurs to operation.

Step S215

When the US signal auxiliary control section 61b senses that the treatment section 9 contacts a metallic instrument based on, for example, the differential value of the current of the HV signal (S15; Yes), processing from step S216 is performed.

Step S216

The US signal auxiliary control section 61b stops the HV signal after 1 ms or less from the HV signal detection.

The US signal auxiliary control section 61b controls the US signal relay 59 to an OFF state (open state). The time period from the detection of the HV signal until stop of application of the US signal to the ultrasound transducer 23 is 1 ms or less.

Here, the reason why it is sensed that the treatment section 9 contacts the other metallic treatment instrument or the like based on the HV signal is that the change of the HV signal is larger than the change of the US signal.

Note that the signal for sensing that the treatment section 9 contacts the metallic instrument is not limited to the differential value of the current of the HV signal detected in the HV signal detection section 62, but may be HV signals detected by various configurations as will be described later.

Step S217

The US signal auxiliary control section 61b keeps the OFF state of the US signal relay 59 until a predetermined US signal output wait time TU of, for example, 150 ms elapses (S217; No).

Step S218

After the predetermined US signal output wait time TU elapses (S217; Yes), the US signal auxiliary control section 61b controls the US signal relay 59 to the ON state (continuity state). Namely, the US signal auxiliary control section 61b controls the US signal output section 50 to restart output of the US signal which is stopped.

Subsequently, the processing from S210 is repeated.

It is only for a short time that the treatment section 9 erroneously contacts another treatment instrument made of a metal, or the like. In the surgical operation system 201, output of the US signal is automatically restarted after the predetermined US signal output wait time TH elapses, and therefore, favorable operability is provided. Note that the US signal output wait time TU is preferably 50 ms to 500 ms, and especially preferably 100 ms to 200 ms. If the US signal output wait time TU is within the above described range, a high-energy discharge does not occur, and no trouble occurs to operation. Note that the reason why the US signal output wait time TU is set to be longer than the HV signal output wait time TH is that as compared with electric energy (HV signal), mechanical energy (US signal) has a low effective response speed, and by stopping for a short time, a high-energy discharge is unlikely to be prevented. Namely, even when application of the US signal to the ultrasound transducer 23 is stopped, vibration of the treatment section 9 does not immediately stops.

Step S219

Until the treatment is finished (S219; Yes), the processing from step S210 is repeatedly performed.

As in the above description, the surgical operation system 201 includes the exclusive HV signal auxiliary control section 51b for performing control that stops output of the HV signal at a high speed when the treatment section 9 separates from tissue, and the exclusive US signal auxiliary control section 61b for performing control that stops output of the US signal at a high speed when the treatment section 9 contacts a metallic instrument.

In particular, in a laparoscopic surgical operation which has increasingly become prevalent in recent years, the probe needs to be operated on tissue that is held by a metallic forceps and a metallic clip in an extremely limited movable range. The surgical operation system 201 can efficiently perform a treatment by the synergetic effect of ultrasound vibration and a high-frequency current, and suppresses occurrence of a high-energy discharge even if the treatment section 9 separates from tissue, or the treatment section 9 contacts a metallic instrument.

Therefore, there is no fear of deterioration of the treatment section 9 being accelerated, and the treatment section 9, the other treatment instruments or the like being damaged, due to occurrence of a high-energy discharge. Therefore, the surgical operation system 201 has favorable operability.

Note that as the configuration examples of using the HV signal auxiliary control section 51b and the US signal auxiliary control section 61b in high-speed control, the same configurations as the surgical operation system 1 or the surgical operation system 201 can be used.

Modification of the Third Embodiment

Figure 19:
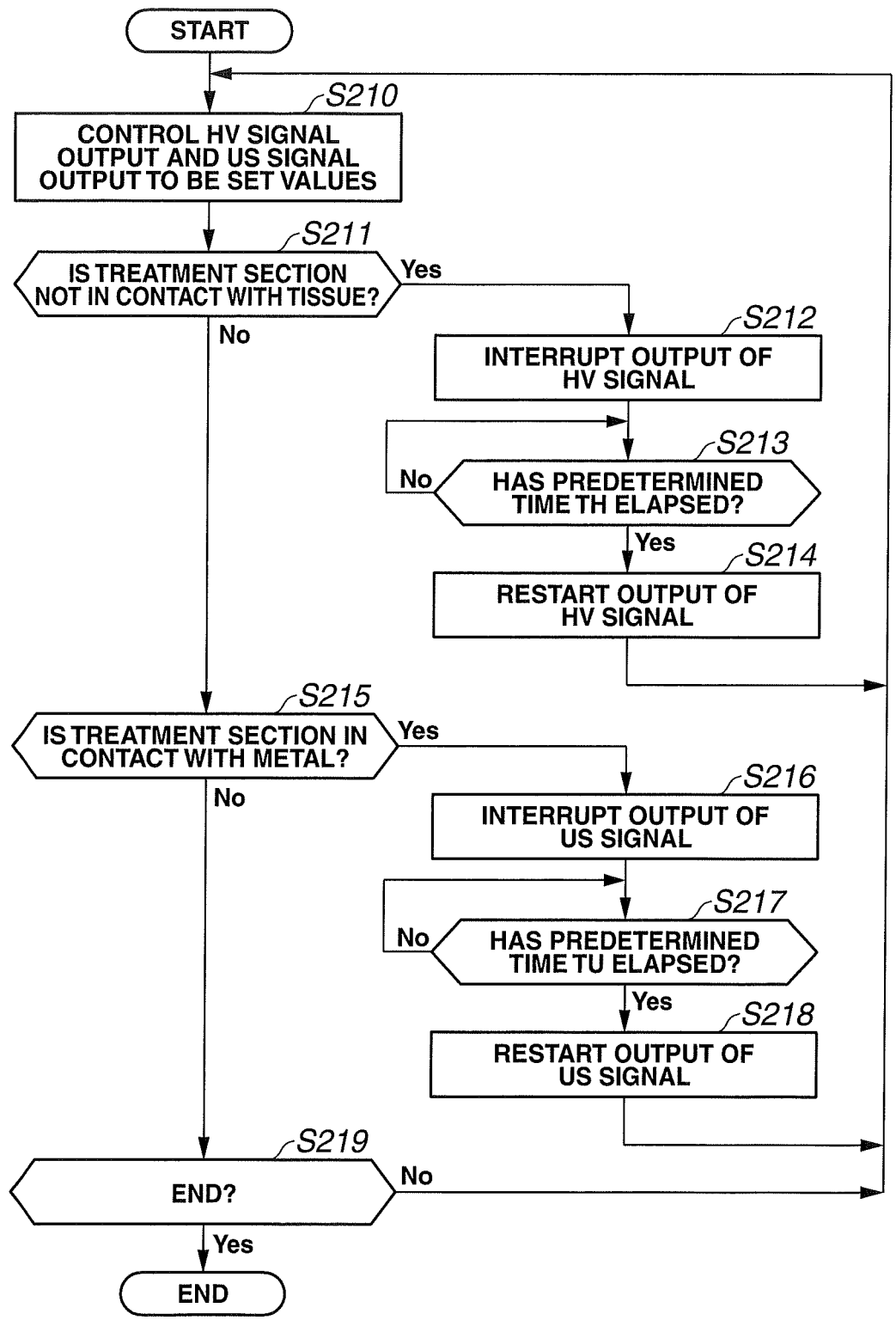
FIG. 19 is a flowchart for explaining a flow of processing of the surgical operation system of the third embodiment.
Figure 20:
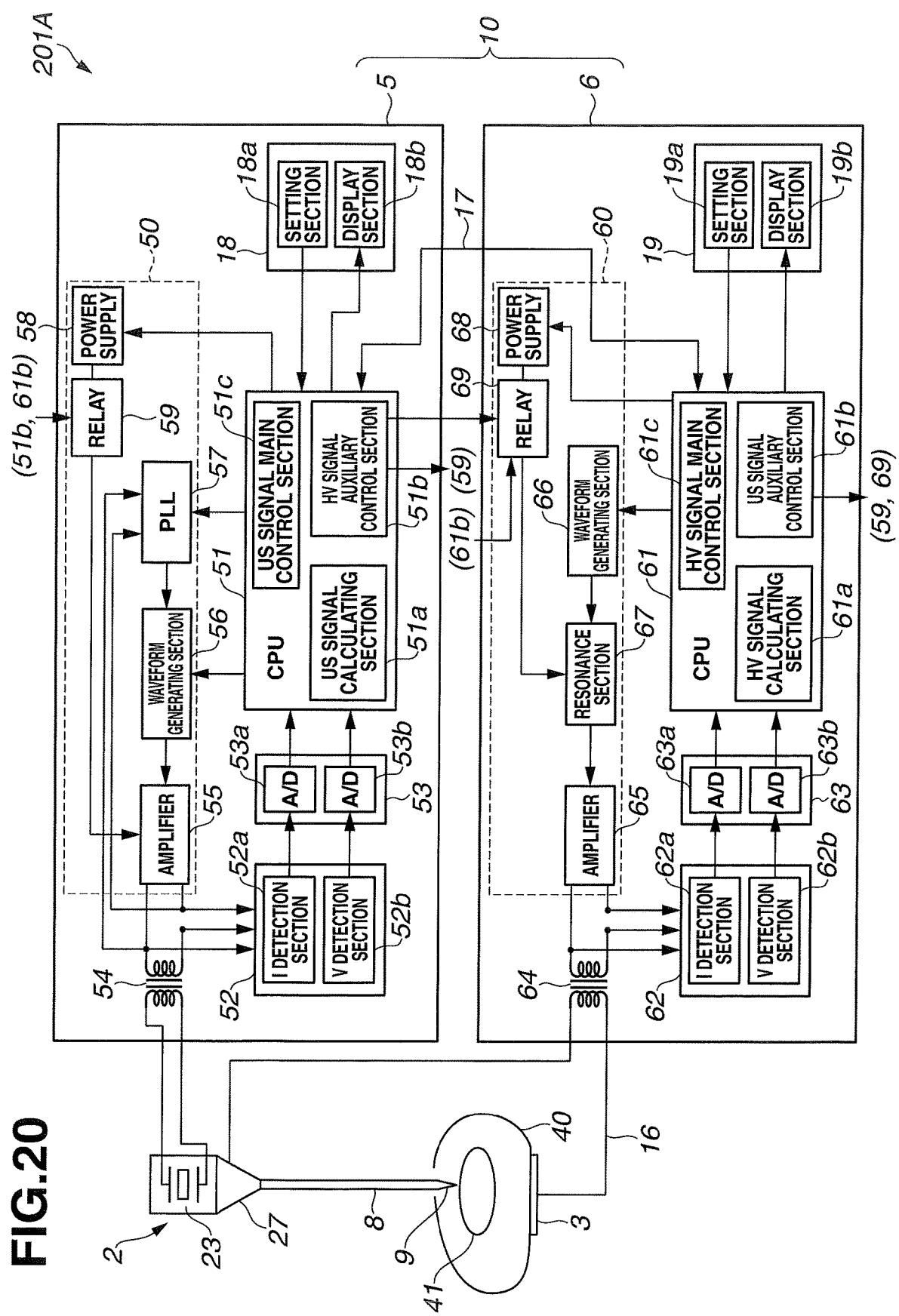
FIG. 20 is a configuration diagram showing a configuration of a surgical operation system of a modification of the third embodiment.

Next, a surgical operation system 201A of a modification of the third embodiment will be described. Since the surgical operation system 201A of the present modification is analogous to the surgical operation system 201 of the third embodiment as shown in FIG. 19, the components with the same functions are assigned with the same reference signs, and the description thereof will be omitted.

The HV signal auxiliary control section 51b of the surgical operation system 201A also performs control that stops output of the US signal simultaneously with control that stops output of the HV signal when the treatment section 9 separates from tissue. Further, the US signal auxiliary control section 61b of the surgical operation system 201A also performs control that stops output of the HV signal simultaneously with control that stops output of the US signal, when the treatment section 9 contacts another instrument made of a metal.

The HV signal auxiliary control section 51b controls not only the HV signal relay 69 but also the US signal relay 59. Further, the US signal auxiliary control section 61b controls not only the US signal relay 59, but also the HV signal relay 69.

The surgical operation system 201A has the effect which the surgical operation system 201 has, and further can more reliably prevent occurrence of a high-energy discharge. Namely, the surgical operation system 201A is more favorable in operability than the surgical operation system 201.

Note that the HV signal auxiliary control section 51b preferably controls the US signal output section 50 so as to restart the output of the US signal which is stopped after the predetermined US signal output wait time period, in the same way as the HV signal auxiliary control section 51b controls the HV signal output section 60 to restart output of the HV signal which is stopped, after the predetermined HV signal output wait time period. Similarly, the US signal auxiliary control section 61b preferably controls the HV signal output section 60 to restart the output of the HV signal which is stopped after the predetermined HV signal output wait time period, in the same manner as the US signal auxiliary control section 61b controls the US signal output section 50 to restart the output of the US signal which is stopped, after the predetermined US signal output wait time period.

The present invention is not limited to the embodiments described above, and various modifications, alterations and the like can be made within the range without departing from the gist of the present invention.

The present application is based upon and claims the benefit of U.S. Patent Application Nos. 61/536,779 filed in the U.S.A. on Sep. 20, 2011, 61/536,796 filed in the U.S.A. on Sep. 20, 2011, 61/536,818 filed in the U.S.A. on Sep. 20, 2011, the entire contents of which are incorporated in the description, claims and drawings of the present application by reference.

What is claimed is:

1. A method for incising a parenchyma organ with low impedance using a surgical operation system including a treatment portion, the method comprising:
   simultaneously applying a high-frequency signal and an ultrasound vibration to the treatment portion;
   bringing the treatment portion close to the parenchyma organ;
   denaturing the parenchyma organ around the treatment portion into a coagulated tissue with high impedance by the high-frequency signal, of the simultaneously applied high-frequency signal and ultrasound vibration, of a coagulation waveform applied to the treatment portion, the high-frequency signal being capable of causing moisture of the parenchyma organ to be vaporized but being incapable of causing the parenchyma organ to be transpired;

causing a low impedance tissue to be exposed, by pressing the treatment portion that performs ultrasound vibration, of the simultaneously applied high-frequency signal and ultrasound vibration, to the coagulated tissue and exfoliating the coagulated tissue in a pressing direction; and transpiring the low impedance tissue to incise the low impedance tissue by generating a discharge between the low impedance tissue and the treatment portion by the high-frequency signal, of the simultaneously applied high-frequency signal and ultrasound vibration, applied to the treatment portion.

2. The method according to claim 1, wherein at least the denaturing, the causing and the transpiring are repeatedly performed in an order of the denaturing, the causing and the transpiring.

3. The method according to claim 2, wherein the high-frequency signal having a crest factor of 5 or more.

4. The method according to claim 2, wherein a vibration speed of the ultrasound vibration of the treatment portion is 8 m/sec to 18 m/sec inclusive.

* * * * *